(12) United States Patent
Pellis

(10) Patent No.: US 6,358,190 B1
(45) Date of Patent: *Mar. 19, 2002

(54) ADJUSTABLE ROTATION RADIUS ARTICULATED JOINT FOR GYM MACHINES AND KNEE TUTORS

(76) Inventor: Giancarlo Pellis, Strada del Friuli, 12/4 - 34136 Trieste (TS) (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,204
(22) PCT Filed: Apr. 11, 1997
(86) PCT No.: PCT/IT97/00079
  § 371 Date: Oct. 15, 1998
  § 102(e) Date: Oct. 15, 1998
(87) PCT Pub. No.: WO97/38759
  PCT Pub. Date: Oct. 23, 1997

(30) Foreign Application Priority Data
Apr. 15, 1996 (IT) .......................................... TS96U0011
Mar. 10, 1997 (IT) .......................................... TS97U0012

(51) Int. Cl.[7] ............................. A63B 23/02; A61F 5/01
(52) U.S. Cl. ...................... 482/136; 482/137; 482/139
(58) Field of Search ......................... 482/97, 100, 137, 482/139, 136; 602/16, 26; 16/375; 403/116

(56) References Cited

U.S. PATENT DOCUMENTS 5,020,797 A 6/1991 Burns
5,330,418 A * 7/1994 Townsend et al. ............ 602/16

FOREIGN PATENT DOCUMENTS

| EP | 0 361 405 | 4/1990 |
| FR | 2 550 708 | 2/1985 |
| WO | WO 84/03433 | 9/1984 |
| WO | WO 92/15264 | 9/1992 |

* cited by examiner

*Primary Examiner*—John Mulcahy
(74) *Attorney, Agent, or Firm*—Browdy and Neimark

(57) ABSTRACT

This invention can be profitably employed in the fields of medicine and sports in the machines used to strengthen the muscles of the knee and in knee tutors.

In its simplest version, the articulated joint is formed by two plates (1, 2) which can move freely on one another; alternatively, one plate (1) or the other (2) can be fastened to a fixed structure by means of a fastener.

One of the plates features two openings (2.2, 2.3), where the first (2.2) is located at the center of a plate and is shaped like a rectangle. The second opening (2.3) has a specific shape: at first it is a circumference whose radius is equal to "I"; subsequently, it is a spiral which returns towards the center of the plate (2).

The other plate features two pins (1.2 and 1.3), located at a distance "I"; the first pin (1.2) is located in the central position and is inserted into opening the (2.2); the second pin (1.3) is in a peripheral position and is located in the second opening (2.3).

Alternatively the plate (2) can be replaced by several overlapping plates (3, 4, 5, 6, 7); the semi-plates are arranged in overlapping couples (4, 7 and 5, 6). The semi-plates (4, 7) are fastened to the plate (3) by means of a pin (4.1) placed in an ideal point of rotation (11) and are therefore free to rotate onto the semi-plates (5, 6).

17 Claims, 19 Drawing Sheets

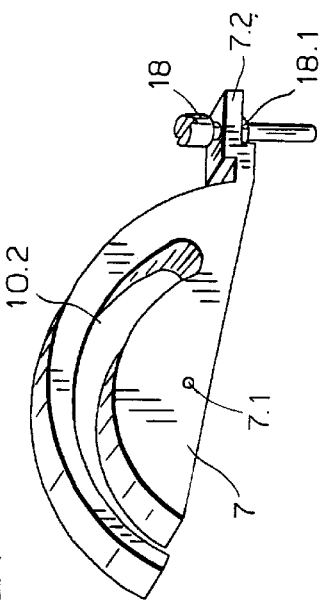 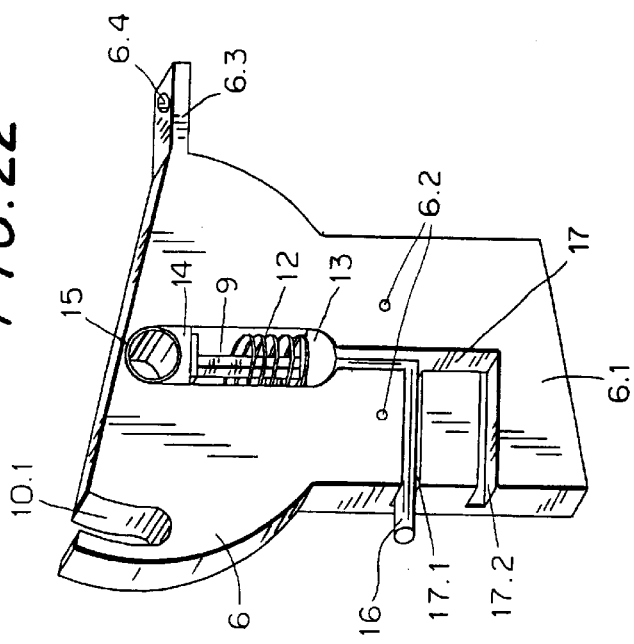
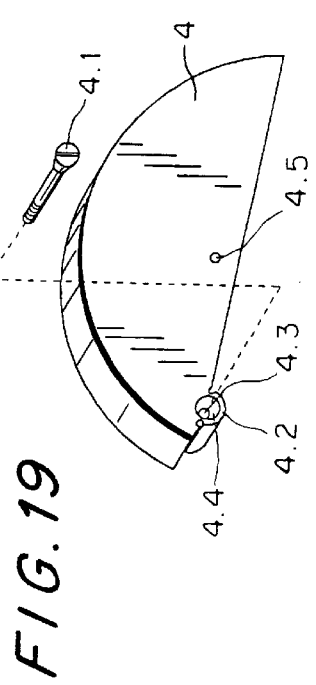 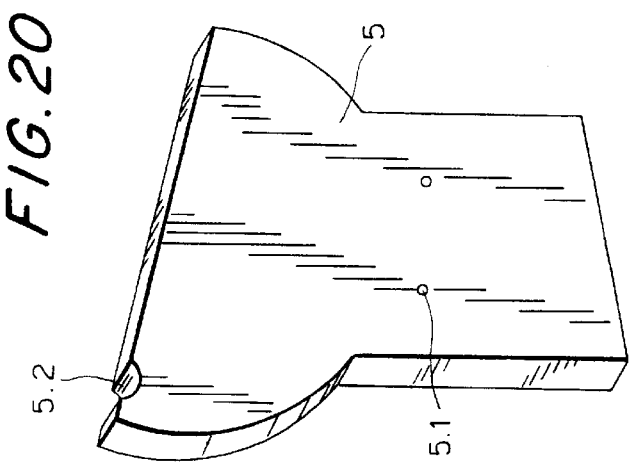
FIG.19  FIG.21
FIG.20  FIG.22

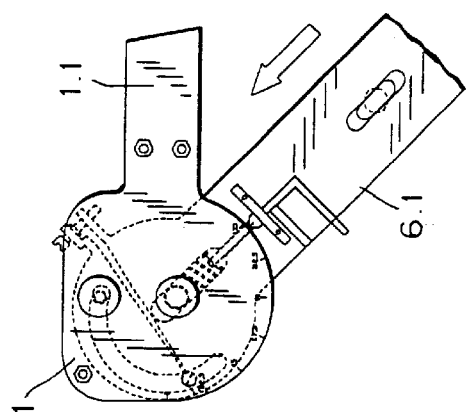
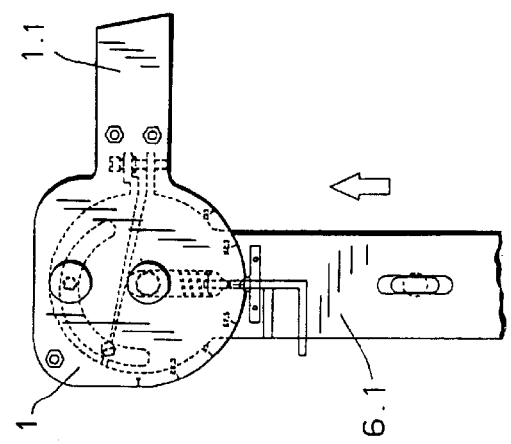
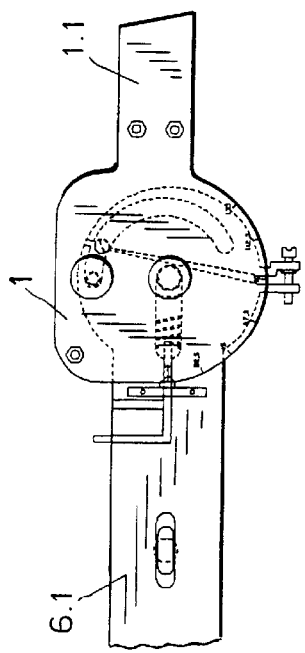

ADJUSTABLE ROTATION RADIUS ARTICULATED JOINT FOR GYM MACHINES AND KNEE TUTORS

TECHNICAL FIELD

This invention can be profitably employed in the fields of medicine and sports as it is an indispensable component of knee tutors and of machines used to strengthen or in rehabilitation to restore the muscles of the knee to their former healthy condition.

The knee is the intermediate articulation of the lower limbs. The movement whereby the knee is extended, or rather, the movement of extending the leg from the thigh is performed by means of the quadricep muscle, which is inserted in the foretuberosity of the tibia, a couple of centimetres below the knee. The movement of bending the knee, that is to say the movement of flexing the leg from the thigh is performed by means of the hind muscles of the thigh, as illustrated in FIG. 1. The flexion-extension movement is always executed at the fore-hind plane.

The particular surfaces that come into contact in the knee are the femoral condyles (the distal, i.e. further, part of the femur), and the tibia plate (the proximal, i.e. closer, part of the tibia), as illustrated in FIG. 2. The femoral condyles consist in round surfaces with a bending radius which is rather narrow but which varies; indeed their profile is very similar to a spiral. The tibia plate, or rather the glenoid cavity of the tibia, has a much wider bending radius than the femoral condyles.

The particular mechanics of the knee is therefore complex, and the type of movement that is made is in direct relation to the angle at which the knee is open. Let us consider an extended leg to be the starting point at a 0 angle. In the first 20°–25° of the bend (i.e.: the angle of ordinary walking) the articulation's mechanics entail a sheer rotation between the two particular surfaces: each point of the femoral condyles is in contact with a corresponding point on the tibia plate. If the flexing continues, in the subsequent 110°–115°, approximately, there is a combined sliding and rotating movement of the tibia with reference to the femur. As the leg flexes further the sliding movement gradually progresses end eventually prevails over the over the rotation and a sheer sliding movement occurs: the femoral condyles slide without rotating on the tibia plate. The knee's ligaments limit the particular caps during these sliding movements and ensure the knee's fore-hind stability, enabling the execution of hinge movements whereby the particular surfaces remain in contact.

Thus, in the flexion-extension mechanics of the knee there is no fixed centre of rotation. When the leg is flexed starting from an extended position, in the first 20° there is a centre of rotation located 60 mm from the tibia's particular surface. However, as the bending movement continues, the point of rotation moves on and, at the same time, the radius grows narrower, until it reaches a minimum distance of approximately 12 mm from the tibia (as can be seen in FIG. 2).

This variation in the radius is transformed into a variation in the distance between a point located in the centre of the femoral condyle which has been identified by tests in the first 20°–25° of the flexion-extension and another point situated on the external malleolus. Indeed, by measuring this distance, experiments reveal that in extending from 135° (position A), to 0° (position B), the variation can increase from 15 to 40 mm (distance $R_B$–$R_A$), as can be seen in FIG. 3. The extent of the variation depends on the conformation of the knee in question.

With reference to physiotherapeutic or rehabilitation problems, when it is necessary to support and follow the knee in its movements, one usually resorts to particular mechanical devices which are strapped to the thigh and leg by means of a system of belts (a sling) which guide the articulation in its movements.

These devices are used in knee tutors, in the machines used for passive gymnastics, and in the gym machines for specific muscle training known as leg curl and leg extension machines.

These mechanical devices, which are thus bound to the limb, are hinged to an articulated joint which generally has a fixed centre of rotation and which is unable to provide the combined sliding and rotating movements and change the centre of rotation, thereby producing anomalous tensions. The latter are caused by the different trajectories of the articulated joint's mechanical devices (circle arc) compared to the one theoretically accomplished by the leg (spiral arc). Indeed, as previously described, the leg reduces its radius when it flexes ($R_B$–$R_A$); this causes the mechanical device to rub against the leg, bringing about a friction which is passed on to the belts of the sling and results in a compressive force.

When the leg is extended, the mechanical device tends to constrict the leg along a circular path, while the leg reduces its rotation radius, and therefore tends to be drawn away from the knee. These compressive and tractive forces, which are proportional to the speed of the movement and to the distance of the knee sling, are then released on the knee caps on the articulation's cartilage (compressive force), and on the knee's ligaments (tractive force) respectively.

The most sophisticated versions of knee tutors currently used in sports feature a complex articulated joint which does indeed try to simulate the compromise between the rotation and sliding movements that typically occur in the knee.

Attempts to solve this problem have been described in the European Patent Application No. 89117781.8 published under No. 0 361 405, in the International Patent Application PCT/US92/01929, published under No. WO 92/15264, and in the International Patent Application PCT/US84/00336 published under No. WO 84/03433.

The knee joint described in the European Patent Application No. 89117781.8 is based on the physiological concept whereby the flexing of the knee consists in the fore movement of the femoral condyles with reference to the tibia condyles, followed by a sheer rotation between the condyles of the above mentioned bones. This joint features three plates, of which the two outer ones feature coaxial holes, while the inner one features two openings where a pair of pins that fit through the above mentioned holes in the outer plates are lodged and guided. One of the openings is small and extends transversally across the longitudinal axis of the tibia and femur, while the other opening is large and is shaped like a circular segment with one end growing wider towards the top.

The first opening, is linear and has the function of reproducing the first fore movement of the femur with reference to the tibia, while the second opening serves the purpose of guiding the subsequent rotation movement.

The upper end of the circular opening is placed on the extension of the longitudinal axis of the arm of the central plate which passes through the centre of the pin lodged in the linear opening, precisely when the pin is halfway through the stroke performed by the pin inside this opening. The centre of the circular segment that constitutes the circular opening consists in the centre of the pin lodged in the linear opening when the pin itself is at the end of the said opening, which is the one farthest from the circular opening.

When the leg flexes, in the first 25° the pin lodged in the circular opening compels the pin in the linear opening to move from its starting position (closer to the circular opening) to its final position (at the end of the linear opening that lies farthest from the circular opening).

As the distance between the centres of the pins is equal to the radius of the circular opening, in this first part of the movement performed by the pin lodged in the linear opening, the pin lodged in the circular opening performs a small vertical movement within and outside the widened part that constitutes the upper part of the circular opening. In this first phase of the flexing movement the two outer plates slide forward with respect to the inner plate (traction or pulling apart phase of the two plates).

Subsequently the two outer plates rotate onto the inner one as the pin at the end of stroke position in the linear opening acts as a fulcrum and compels the pin lodged in the circular opening to move (sheer rolling phase). The joint described in the International Patent Application No. PCT/US92/01929 features an improvement of the afore described European Patent Application No. 89117781.8. As in the previous case, at first there is a horizontal translation of the pin lodged in the linear opening for an angle α1 of approximately 25°–35° of the flexing movement, with the leg outstretched in the starting position. As a result, the tibia is made to slide back with reference to the femur. In this joint too in the first phase of the flexing movement the pin lodged in the circular opening moves up and down by a Y quantity at the upper end of the circular opening when the pin lodged in the linear opening passes through the latter.

This first phase of the movement is the followed by a second phase for an angle α2 which goes as far as 120°–135° of the flexing movement. This second phase is characterised by an essentially single-centred movement: the pin, which at the end of the stroke is positioned in the linear opening acts as a fulcrum and compels the pin lodged in the circular opening to translate inside the latter.

Compared to the European Patent Application No. 89117781.8, the improvement of the present joint consists in the attempt to modify the shape and/or the position of the openings whenever the conditions of a given patient make this advisable.

The bend of the circular opening which extends beyond 35° of the flexing movement is thus made flatter and the linear opening is extended slightly towards the distal (i.e. further) end from the circular opening. In the first phase of the flexing movement (from 0° to 25°, angle α1), the pin lodged in the linear opening moves distally, as a result of which the tibia is made to slide behind the femur during this first phase. Subsequently, from 25° to 35° of the flexing movement (angle α2) the latter pin stays still and thus will constitute the fulcrum around which the pin inside the circular opening will rotate.

Lastly, from 90° to approximately 135° of the flexing movement (angle α3), the pin in the linear opening will be forced to draw closer to the circular one when the other pin moves downwards in the flattened part of the circular opening, thereby producing a multi-centred movement in which the tibia moves in front of the femur.

Even without engaging in a controversy with the inventor of the above mentioned Patents with reference to his conceptual hypothesis on the physiological movement of the knee, it must be said that although his Patents have attempted to tackle these kinds of problems they have not succeeded. The basic model of the joint he has invented is based on the initial movement of the pin lodged in the linear opening in all its length and simultaneously on the upward and downward movement (Y) of the other pin. Indeed, in its basic model the joint features two centres of rotation. In the first phase of the movement between the plates the centre is the pin lodged in the circular opening.

Where as in the second phase of the flexing movement (between 25° and 135°), the centre is the pin that is lodged in the linear opening.

By applying this mechanical principle inside the knee, one might suppose that the latter functions with a series of jerks. This is far from true, as the movement that occurs between the particular caps features no jerks at all and is mostly a rotation movement onto which a sliding movement progressively prevails.

The movement performed by the plates is not continuous. The personalisation of the curve for each individual patient is therefore absolutely uncertain.

The knee tutor joint described in the International Patent Application No. PCT/US84/00336 consists of 5 plates. The two outer ones, connected to the supporting elements of the lower leg, each feature a hole and a linear opening. The two intermediate plates also feature a hole and a linear opening each, but in the opposite position compared to the holes and openings of the outer plates.

The central plate, which is connected to the supporting elements of the upper leg, features a central hole and a bending opening which extends completely within the plate itself and which simulates the crosswise course of a flexing point on a given patient's knee.

The plates are locked onto one another and they can each pivot around one another and around the central shaft. This shaft extends through the linear openings in the outer plates and the central holes of the intermediate and central plates.

A pin passes through the peripheral holes of the two outer plates, the linear openings in the intermediate plates and the bending opening of the central plate.

The central shaft and the pin lock the plates onto one another in such a way that the restricted movement of the pin inside the bending opening limits the movements of the supporting elements of the lower leg with respect to those of the upper leg: hence, the flexing and extension of the patient's lower leg is limited.

The bending opening lodges some flexible pistons, which act as springs. These can move and are fastened to the ends of the bending opening in order to limit the movement of the pin and, consequently, the width of the flexing movement. These flexible pistons are locked by two threaded bolts next to each of which lies an indicator that moves longitudinally to the pistons themselves. The function of the indicators is to indicate the degrees of movement allowed in the flexing and extension movements: from 0° to 140°.

If one postulates that the central plate stays still, in this joint the intermediate plates rotate and move with respect to the central one. The outer plates rotate along with the intermediate ones but they move to the side of the latter plates along the axis in the direction of the linear openings in the intermediate and outer plates. In this system the outer plates move (rotate and slide) with respect to the central plate.

The central shaft and the pin that passes through the peripheral holes of the outer plates also change distance between them in the flexing movement. However, there is no prior identification of the centre of the knee; this centre ought to be aligned with the central shaft. Furthermore, the possibility of personalising the bending opening is not described other than by referring to the extreme limits imposed on the movements.

In the machines currently used for passive gymnastics, the hinge rotates around a fixed centre and cannot accompany the flexion-extension movement with a physiological trajectory. Hence, anomalous tractive and compressive tensions are formed and released onto the ligaments.

Gym machines are used to strengthen groups of muscles in a voluntary way.

As previously mentioned, the machines currently used for the muscles in the knee are the leg curl and leg extension machines. The former selectively strengthens the knee's flexor muscles, while the latter focuses on the extensor muscles.

A leg extension machine is very similar to a rather high chair. When seated upon it the feet cannot touch the ground and the thighs are bound to the seat by means of straps or other constraints. A mobile load arm L (FIG. 4) is located in the centre of the seat, or beside it (see FIG. 5), and runs vertically, along the longitudinal axis of the leg, rotating around a fixed centre C, which constitutes the fulcrum of the entire system. Its rotation axis "c" ought to correspond to the horizontal axis which passes through the femoral condyles (which is believed to be the centre of the knee).

An orthogonal rod M is attached to the distal part of this mobile arm L, and the distal part of the leg exerts pressure on this very rod. The leg's extension from the thigh, which makes the arm L rotate around axis "c" is countered by the load of weight P, featured in the machine. This weight P can be connected by means of a transmission system (ropes and pulleys) to the mobile load arm L itself (as can be seen in FIG. 4), or to a rotation mechanism (FIG. 5). In the latter case, a driver shaft N (with a rotation axis that coincides with the above mentioned "c" axis) connects the mobile arm L to the articulated joint.

When the lower part of the leg extends, with the thigh bound to the machine's seat and the lower part of the leg free to move, mechanical shear and bending stresses are exerted.

When the flexion-extension movement of the lower part of the leg occurs, a number of rebound phenomena take place which are proportional to the load (weight P) and to the velocity with which the load itself is lifted.

In order to avoid exerting these stresses, especially in patients who have just undergone surgery in the crossed ligaments, the lower part of the leg should also be bound in several points by some sort of sling (see FIG. 7), so as to make it as integral as possible to the mobile load arm L. The latter, which is hinged to the frame of the gym machine, releases rebound phenomena on the central rotation pin, thereby safeguarding the crossed ligaments.

The major flaw in the machines currently on the market lies in the fact that the leg cannot be made to rotate around a fixed centre because the knee, as previously stated, has no single centre of rotation and therefore cannot, as it moves, run along a circular path, but rather must perform a spiralling movement towards the centre. Hence, if the limb is fixed to the mobile arm L of the machine, it exerts its rotating movement onto the leg, tugging it as it flexes when the leg gradually reduces the radius of its trajectory, and, vice versa, compressing it as it stretches, thereby creating anomalous tensions which are released on the crossed ligaments, the knee caps and the particulatory cartilage.

In this specific sector some devices are known to exist that are capable of reducing the tensile stresses exerted on the leg. The one described in U.S. Pat. No. 5,020,797 is aimed at allowing a leg injured in the knee to exercise, by applying a resistance force onto the leg. The leg can be extended against this resistance in a given direction, at the same time it is able to prevent a sub-dislocation in another direction close to the knee.

This device includes a fastening device connected to a mobile arm which, in turn, is connected to an exercise machine, two shafts, each with its own fulcrum, connected to the above mentioned device, a sling connected to the fastening device to perform a pivoting movement around the first shaft, and another sling that is also connected to the fastening device for pivoting around the second shaft and a lever mechanism.

The latter features an upper arm connected to the first sling, a lower arm connected to the second sling, and a lever coupling in proximity to the adjacent ends of the above mentioned arms used to pivot.

The first sling is connected to a protruding part of the upper arm of the lever. One must first apply a supporting force in one direction next to one end of the above mentioned first bone, as this first end is close to the above mentioned articulation. The second sling is connected to a protruding part of the lower arm of the lever. This is where a second resistance force is to be applied in another direction close to another end of the above mentioned first bone.

This device serves the purpose of avoiding a sub-dislocation through means that are applied next to the lower part of the leg. It is entirely unrelated to leg tractions having the knee as the fulcrum.

Indeed, this patent enables the tibia to advance "properly" in the extension movement which turns out to have been "proper" only when the starting position is "improper", that is to say if the centre of the knee is set back (but not excessively so) with reference to the centre of the machine. Should the centre of the knee be casually placed (indeed, no description of how to identify it is available) and therefore be aligned to the centre of the machine or advanced, the above mentioned system brings about the advancement of the tibia and exerts a stress on the fore crossed ligament.

Another device known to exist is described in the French Model No. 83 13474 published under No. 2.550.708, which allows the reduction of the pressure in the knee's joint when exercising the quadriceps muscles. This device features an arm endowed with weights pivoted onto a joint, a horizontal shaft that passes through the joint itself and a load arm. Special slings keep the patient still on a chair so that one thigh is fastened. The rod of the load arm is replaced by a special fastening shoe which features fastening strips whereby the patient's foot is locked to the shoe itself. The latter is locked onto a staff which is connected to the free end of an arm that constitutes a part of a three-arm lever that can rotate around the shaft.

One of the three arms consists in an indicator that shows on an angular scale the traction or rotation movement of the foot. The said scale is rigidly borne by a sleeve, which can be moved to the resistance arm in an arbitrary position by means of a screw. An elastic component is mounted on a pin which in turn is rigidly fixed to the said sleeve.

When the patient is exercising the quadriceps muscle and extends the leg, making the foot notate upward the immobilising shoe is pulled upward. This exerts a tensile stress on the foot of the patient. This traction or rotation movement brings about a compression of the elastic component. The width of the compression, which depends on the upward movement of the shoe, is indicated in the angular scale of the above mentioned indicator.

Hence, traction occurs in the longitudinal direction of the lower part of the leg, pressure in the articulation of the knee diminishes and no pain is felt in the knee when taking exercise. The traction is brought about automatically when the patient extends the leg or moves the lower part of it around the articulation of the knee. The width and the variation of this traction depend both on the characteristics of the elastic component and on the distance between, the trajectory of a point that coincides with the fastening elements of the lower part in the patient's leg rotating around the articulation of the knee, and, the trajectory of a point that coincides with the immobilising shoe rotating around the axis of the same joint (that is to say, the distance of the position of the rotation axis of the load arm with reference to the position of the articulation of the knee).

By placing the rotation axis of the load arm of this training device forward and above the articulation of the knee, it is possible to vary the traction curve in such a way that the maximum traction is achieved for a pre-established position (angular) in the movement between the position where the knee is completely bent (90°) and the one where it is completely extended (0°).

By placing the two axis eccentrically in a given position with reference to one another the traction force can be made to increase gradually with the pressure in the articulation.

This device constitutes an attempt to solve the problems related to moving the knee by using a lever mechanism which is applied to the patient's foot. It rightly assumes that the alignment between the rotation axis of the device's load arm and the rotation axis of the articulation of the knee is essential, but instead of acting on the knee itself it tries to increase the tensile stress on the articulation.

This last patent brings about a traction of the calf with respect to the thigh during the flexion-extension. This occurs in order to counterbalance the cohesive stresses caused by the quadriceps muscle which can contract painfully. The modulation of this tension occurs by placing the centre of the knee in correspondence to the centre of the machine. Hence a system for the exact identification of the centre of the knee is required.

The problem then consists in accompanying the knee while it moves without allowing other mechanical stresses to interfere in its movement. In this case, once again, we have no personalisation of the trajectory even though each subject has his or her own flexion-extension trajectory.

In conclusion it can be said that each one of the examined patents has made an attempt to find a solution to a given atypical problem observed in the flexion-extension mechanics of the knee.

None of the inventors has thus addressed the issue by making considerations which would connect all these phenomena and identify a common denominator. This very common denominator can be found in the definition of an efficient methodology for the assessment of the articulation which must, initially, envisage the identification of an anthropometric point of reference, and subsequently its alignment with a measuring device. This point must always be found in as much as it is essential not just for a correct assessment but also to align properly any device to be connected to the knee itself (knee tutor, passive gymnastics machines, gym machines).

Furthermore, the definition of an efficient methodology enables the correct identification of the trajectory made by the knee in the flexion-extension, a trajectory which must be accompanied by a drawing of the particular surfaces of the tibia and femur and the succession whereby the rotation and sliding movements are combined.

The above considerations hold true with reference to an average knee. However, the length of the crossed ligaments, their proportions and their point of insertion (features which characterise particular surfaces), differ considerably from one individual to the next. This means that the spiralling movement made by the knee differs in every individual. In order to examine the actual particular profile of a given knee it is therefore necessary to take X-rays or to measure the distance between the knee and the malleolus of the individual at different degrees of flexion.

DISCLOSURE OF INVENTION

The purpose of this invention is to provide users with an articulated joint endowed with a mobile arm L that is capable of guiding the flexion-extension movements of the leg along a trajectory which reproduces as naturally and as faithfully as possible the movement that is performed by the knee's particular surfaces: sheer rotation, sliding-rotation and sheer sliding. Another aim is that of creating a device that can easily be modified, so that it may be adapted to the anthropometric characteristics of each subject.

These and other objectives are indeed achieved by this invention, which consists in a joint with a variable and controllable rotation radius to be installed in gym machines (leg extension and leg curl), on machines for the passive gymnastics of the lower limbs, and on knee tutors (knee guides). In its simplest version, this articulated joint consists of two mechanical parts such as plates each of which is attached to an arm.

These two plates move freely upon one another when neither is locked to a fixed structure. Alternatively, a plate is fastened to a fixed structure by means of its own arm and the other plate rotates upon itself, that is fixed to the mobile plate is mobile arm L.

Both plates can be unlocked when the articulated joint is used in knee tutors and in passive gymnastics machines, where the thigh and leg move simultaneously. The articulated joint with one of the plates locked is recommended in the leg extension and leg curl machines, where the thigh is bound to the seat of the machine and the flexion-extension movement can only be performed by the leg. When the plate arms are bound to the thigh and calf the hinge lies at the level of the knee.

According to the type of transmission used for the load (weight P) of the machine, two cases may occur: an articulated joint with two plates and with the load applied to mobile arm L, or an articulated joint with the load applied to the pin of the joint itself.

One plate is free to rotate onto the other plate with reference to a horizontal axis "c" which must correspond to the axis of the femoral condyles of the subject when seated.

One plate features two openings at a right angle to the rotation surfaces of the plates. The first opening is located in the centre and develops lengthwise; this opening begins from a central point located in the centre of the plate and then proceeds towards the mobile arm L along a radius (a) whose direction coincides with the longitudinal axis of symmetry of the mobile arm itself.

The ends of the second opening, located peripherally, should preferably be rounded. The centre of one of the ends of this second opening is located at a distance "I" from the centre of the above mentioned central point, and lying on radius "b", at a right angle to radius "a" and on the same plane. The centre of the other end of the second opening is located at 130°–140° with reference to radius "b".

The second opening has a specific shape: initially, for the first 15°–45° with reference to the above mentioned radius "b", it has a circular form whose centre coincides with the central point and whose radius is equal to "I"; for the remaining 90°–120°, it has a spiral form which develops towards the central point. The sequence of points forming the longitudinal axis of this spiral is derived from the sequence of points of one end of a segment of length "I", the other end moves along the longitudinal axis of the central opening.

Alternatively, the above mentioned peripheral opening can also consist in a opening having a similar shape, with its cavity facing the rotation surface of the plates.

The other plate features two pins whose longitudinal axis are at a right angle to the rotation surfaces of plate itself. These pins are located at a distance equal to "I". The first pin is inserted into the above mentioned central opening; the second pin is placed in the peripheral opening.

The pins feature at the distal end, a constraint which prevents the two plates from separating. Should the peripheral opening be replaced by a opening, the second pin will not pass right through and will feature no constraint on its distal end.

Actually, the plate endowed with pins can either be the one locked to the gym machine or the one that is free to rotate on the former. Furthermore, it is possible for each plate to feature opening and only one pin, provided that they alternate: one plate will feature one opening and a pin which will be lodged in the opening of the other plate.

When the load of the gym machine is transmitted to mobile arm L by means of a driver shaft, the latter takes the place of the central pin. The longitudinal axis of the driver shaft is located on the extension of axis "c" of the knee; this driver shaft act's as fulcrum for a plate and for its mobile arm L, the other plate is fastened to the machine.

The unlocked plate, with the mobile arm L features the above mentioned linear central opening.

In this case the central pin driver shaft is endowed at its end with a feather key lodged in the central opening. In order to prevent the central pin/driver shaft from sliding out of the central opening, the latter features (in proximity to the feather key) a threaded area onto which a bolt or other stoppage is screwed.

The length of this opening is increased vertically according to the size of the feather key, whose point of symmetry (where the transverse and longitudinal axis meet) must coincide with the central point.

The plate fastened to the machine by means of a fastening arm is crossed by a hole whose centre corresponds to the central point, where the central pin/driver shaft is to be lodged and allowed to rotate freely.

By means of the feather key located at one end of the driver shaft, inserted in the central opening, the load is transmitted to the mobile arm L. A second pin is fastened to plate and lodged in the peripheral opening on the other plate.

Even though suitable for an "ideal" knee, an articulated joint thus made cannot be adjusted to the anthropometric characteristics of each individual. Consequently, each knee requires a plate of its own, with a suitable peripheral opening.

In other to make the articulated joint more versatile, one of the plate is replaced by another plate that acts as a cover and by a group composed of one plate A and by segments of plates B, C, D, E.

The segments of plates are arranged in pairs when one pair is placed side by side to the other pair. In each pair one segment is put on top of the other. In the group, the segments of plates are connected to one another and to the plate.

The group is free to rotate between the above mentioned two plates with reference to a horizontal axis "c", which must correspond to the one crossing the femoral condyles of the subject when seated.

The group can be unlocked as is the case in knee tutor and/or in machines used for passive gymnastics.

When applying the articulated joint with multiple plates/segments of plates to leg extension and leg curl machines, two version are possible, according to the type of transmission of load features by the machine. The following two cases are possible: an articulated joint with multiple plates/segments of plates with the load on mobile arm L, or an articulated joint with multiple plates/segments of plates with the load on the pin of the joint.

In an articulated joint with multiple plates/segments of plates used a gym machine in which the load is applied directly to the mobile load arm, one of the plate is constrained by a fastener, such as an arm on the leg extension and leg curl machines. The plate that acts as a cover is in turn fastened to this first plate. The group is inserted between the locked plate and the cover plate.

These segments of plates B, C, D, E, have a particular conformation. The segment of plate D, which is close to the plate fastened to the gym machine, features the previously described linear central opening. Plate A or one of the segments of plates C, D is possesses an arm that is the mobile arm. L. When the two segments of plates D, E, which are closer to the plate locked to the gym machine, are put one on top of the other, they feature the previously described peripheral opening, whose radius "d" divides the opening in two parts: one containing the circular part and the other containing the spiral part. Fulcrum is located on radius "d".

The above mentioned segments of plates B, C, D, E, are cut according to axis "e" which goes from this fulcrum to the point of intersection of radius "f" with the outer edge. Radius "f" is diametrically opposite radius "b".

These segments of plates B, C, D, E, are arranged side by side in pairs B, E and C, D. Their matching edges have not been cut precisely along the axis "e" but rather (considering the above mentioned fulcrum as the starting point), they diverge for a few degrees from axis "e" in the direction of the mobile arm, or in the opposite direction. Hence, a distance is created in correspondence with the intersection of axis "e" with radius "f" between the two pairs of segments of plates (B, C and D, E), this allows the rotation of one pair of segments of plates (B, E) on the other (C, D), around the above mentioned fulcrum. By means of a screw, it is possible to adjust the distance between the two pairs of segments of plates.

In other words, segment of plate B, which is fastened to plate A only by means of the pin located in the above mentioned fulcrum, can rotate with reference to a segment of plate C, which is permanently fastened to plate A. A segment of plate E is fastened to segment of plate B, and a segment of plate D to segment of plate C, a segment of plate E can rotate with reference to a segment of plate D. Given that the segment of plate E features the espiral part of the peripheral opening, the latter's position may vary with reference to the circular part of the peripheral opening itself owing to the rotation around the above mentioned fulcrum.

The locked plate features two holes, one located in the centre, and the other peripherically at a distance equal to "I". In the central hole a pin is inserted which is lodged in the central opening of segment of plate D; this pin simply acts as a fulcrum around which the group of plate and segments of plates rotate. A pin is placed in the peripheral hole and is lodged in the peripheral opening formed by segments of plates D, E.

By adjusting the screw which is connected to plates D, E, it is possible to change the distance between these pairs of segments of plates (B, E and C, D) (as well as the position of the spiral part of the peripheral opening), so that the trajectory rotation of the group on the locked plate (by means of the pins featured by the latter) may correspond as much as possible to the trajectory flexion-extension of the leg of the subject in question.

If the articulated joint with multiple plates/segments of plates is used on a machine in which the load is applied directly to the pin of the joint, the previously described group of plate A and segments of plates B, C, D, E, maintain the same function, even though their position is changed. Plate A and segments of plates C, D are fastened to the machine by means of a fastener, such as an arm, while the plate that was locked and the first pin now moves freely. Segments of plates B, E, being connected to plate A, are also fastened to the machine, but may rotate partially on plate A and segments of plates C, D thanks to the pin located on the fulcrum.

As described previously for the two plate articulated joint where the load is attached to the pin of the joint, the unlocked plate constitutes the proximal part of mobile arm L, and is endowed with the above mentioned central, opening. Furthermore, there is the previously described central pin/driver shaft, featuring the feather key lodged in the linear opening of the unlocked plate, and a threaded area onto which another plate or a bold is screwed, acting as a cover for the entire system.

Plate A and segments of plates C, D are crossed by a hole in which the central pin/driver shaft will be lodged and allowed to move freely.

By means of the feather key, located at one end of the driver shaft inserted in the central opening of unlocked plate the load is transmitted to the mobile arm L. The unlocked plate, in turn, will follow the previously described movement of the peripheral opening on segments of plates D, E, compelled to do so by the presence of the peripheral pin that is fastened to the unlocked plate and lodged in the peripheral opening.

Irrespective of the number of plates or segments of plates and of the fastening system used to bind them to the machine in the proximal part of the mobile arm, an opening is made in which a mechanical hook is inserted allowing it to run along the opening itself. On this mechanical system the sling to be used for the calf will be fastened, approximately below the knee.

Furthermore, the mobile arm features another opening, located distally, wherein a feather key is lodged which is allowed to run freely between axis "a" of the mobile arm itself. The foot rest is attached onto this feather key; a pin can lock the feather key to the mobile arm.

The above mentioned foot rest consists of a blade or plate which is bent at one end at 90°, or by two joined blades or plates united at 90°. The vertical part of the rest is joined to the mobile arm, while the horizontal part is the place where the foot actually rests, locked in position by means of a small belt.

In the gym machines where the load is applied on the pin of the articulated joint, irrespective of whether a two plate or plates and a group of plates and segments of plate is used, the articulated joint can be modified when the central pin/driver shaft is wider than the unlocked plate.

In this case, a guide is milled on the central pin/driver shaft, where the unlocked plate is placed. The central pin/driver shaft, features a longitudinal central threaded hole.

A three-part screw featuring head, body and thread, and whose threaded part is engaged in the threaded hole of the central pin/driver shaft, keeps the unlocked plate within the guide, with its non-threaded section going beyond the central opening. The head of the screw prevents the separation of the two mechanical parts.

When the leg transmits the motion to arm L, which is fastened to the unlocked plate, the proximal part of unlocked plate, which is inserted in the guide of the central pin/driver shaft, transmits this motion to the central pin/driver shaft itself through the contact of the sides of the unlocked plate with the internal surfaces of the central pin/driver shaft guide.

The second pin featured by an unlocked plate, which is lodged in the peripheral opening of the locked plate, makes the unlocked plate and the mobile arm L, which is connected to it, move along a trajectory with a varying radius, parallel to the one of the leg in the sling of arm L.

This variation in the radius during the flexion-extension trajectory of the leg from the thigh makes the unlocked plate within the guide moves; the screw/pin, which in turn is inserted in the central opening and does not hamper this movement.

In using an articulated joint with plates and a group of plates and segments of plates on gym machines, a degree angular scale is to be drawn in an appropriate spot on a plate. The 0° position will correspond to the longitudinal axis of the mobile arm L when the latter is the extension of the arm which joins the device to the machine. The scale develops in the opposite direction in which the peripheral opening is developed.

Parallel to the distal opening in the mobile arm L, on the outer edge or on the side opposite the one to which the leg is fastened, a verification linear millimetre scale is located, whose ideal zero is the central point of the locked plate.

Instead of degree scales, two encoders may also be used to measure the movements simultaneously, one located in the place of the linear scale, the other in the place of the angular scale.

The above mentioned pins inserted in the central and peripheral openings can be ellipsoidal, in order to ease their longitudinal motion within the above mentioned openings; these pins may also be provided with rolling bearings.

The spiral part of the peripheral opening can be divided into several areas, each one featuring its own centre of rotation, using more segments of plates. Hence, it is possible to adjust the position of the above mentioned spiralling part of the peripheral opening even more precisely.

Plate A and segments of plates C, D can consist in a single piece. The segments of plates B, E can consist in a single piece too.

The device which is the object of this patent application can be used on the machines that exist at present and on future machines by removing the traditional rotation device.

It can also be used as an accessory in combination with the traditional mechanism, thereby making the machine more functional. Lastly, the device can also be used as an accessory on other types of machines (or seats), thereby endowing them with the same function as leg extension and leg curl machines. In the latter case, the fastening bar will be locked onto the machine (or onto the seat) by means of those components that are known to achieve this aim.

The use of this invention on gym machines permits the strengthening or re-education of the extensor and/or flexor muscles of the leg with reference to the thigh, so that the anomalous physiological stresses (shear, flex, rebound, tensile and compressive), which occur during motion may be prevented from releasing harmful tensions on the ligaments. Its use in knee tutors (knee guides) similarly avoids that the same types of anomalous physiological stresses be released on the knee's ligaments, on the knee-covers, on the particular cartilage of people who have suffered an injury in their knees, or athletes, as they walk, do sports or perform rehabilitation exercises.

Indeed, this articulated joint provides a solution for the problems featured by the inventions described in the above mentioned patents. Its innovative characteristics, which consist in the position of the central opening that starts at the centre of the plate on the same axis with reference to the lower point of the peripheral opening, and proceeds along the symmetrical axis of the load arm, a constant distance "I" between the pins, and thus a constant distance between the two openings when the pins are in motion, and the rotation around an axis (c) that passes through the femoral condyles of the subject of the plates or segments of plates which allow this joint to reproduce as faithfully as possible the sequence that occurs in the variation of the knee's centre of rotation and the progression of the rotation and sliding movements. Hence, the leg and arm L which is connected to the leg remain on trajectories that coincide perfectly, so that in each phase of the flexion-extension movement there is a perfect correspondence between every point of contact between the leg and arm L. This prevents any kind of slipping between the mechanical device and the limb, thereby avoiding the above mentioned anomalous tensions.

A BRIEF DESCRIPTION OF THE DRAWINGS

Other characteristics and advantages of the invention will be more evident with the description of some specific and preferred but not exclusive configurations of the articulated joint, indicatively illustrated in the enclosed drawings in which:

FIG. 19 shows the first segment of the plate of the mobile group of the articulated joint;

FIG. 20 illustrates the second segment of the plate of the mobile group of the articulated joint;

FIG. 21 shows the third segment of plate of the mobile group of the articulated joint which is placed side by side to one shown in FIG. 19;

FIG. 22 shows the fourth segment of the plate of the mobile group of the articulated joint which is placed side by side with the one shown in FIG. 20;

FIGS. 23, 24 and 25 show three different arrangements of the articulated joint, when the leg is in the extended position, flexed at 90°, and flexed at 135° positions;

MODE FOR CARRYING OUT THE INVENTION

Figure 1:
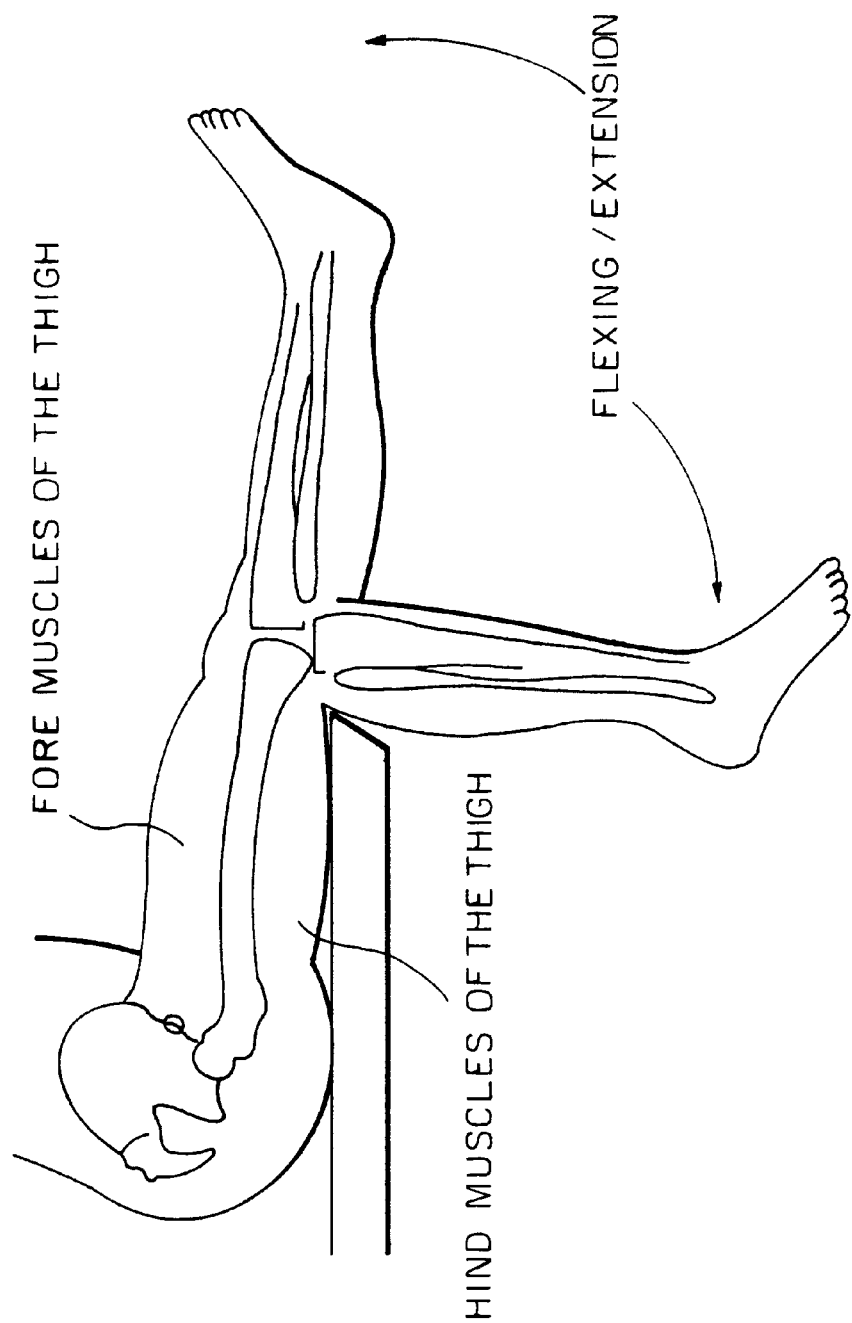
FIG. 1 illustrates the position of the muscles of the thigh and the flexing and extension movements.
Figure 2:
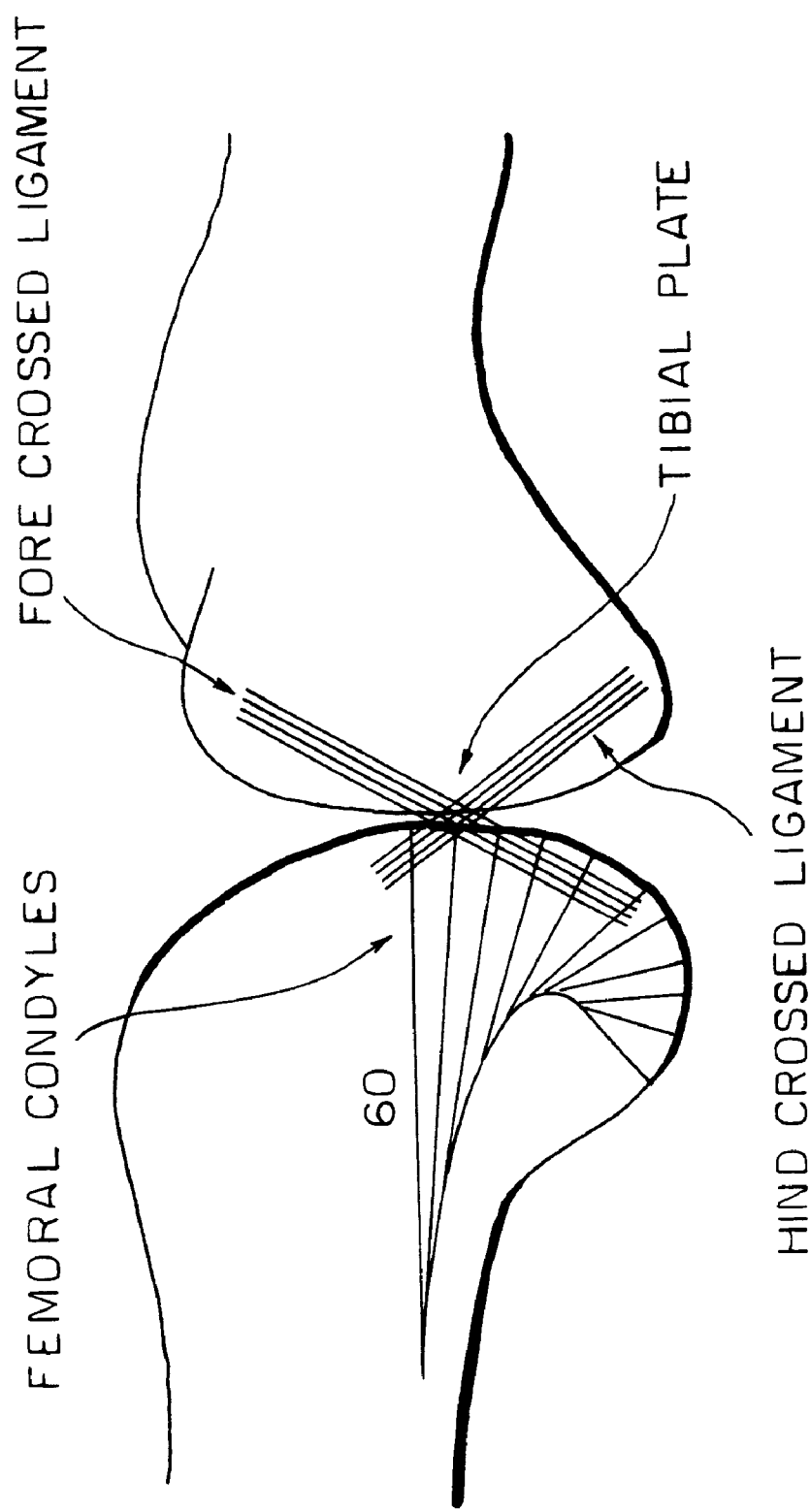
FIG. 2 shows the particular surfaces of the knee.
Figure 3:
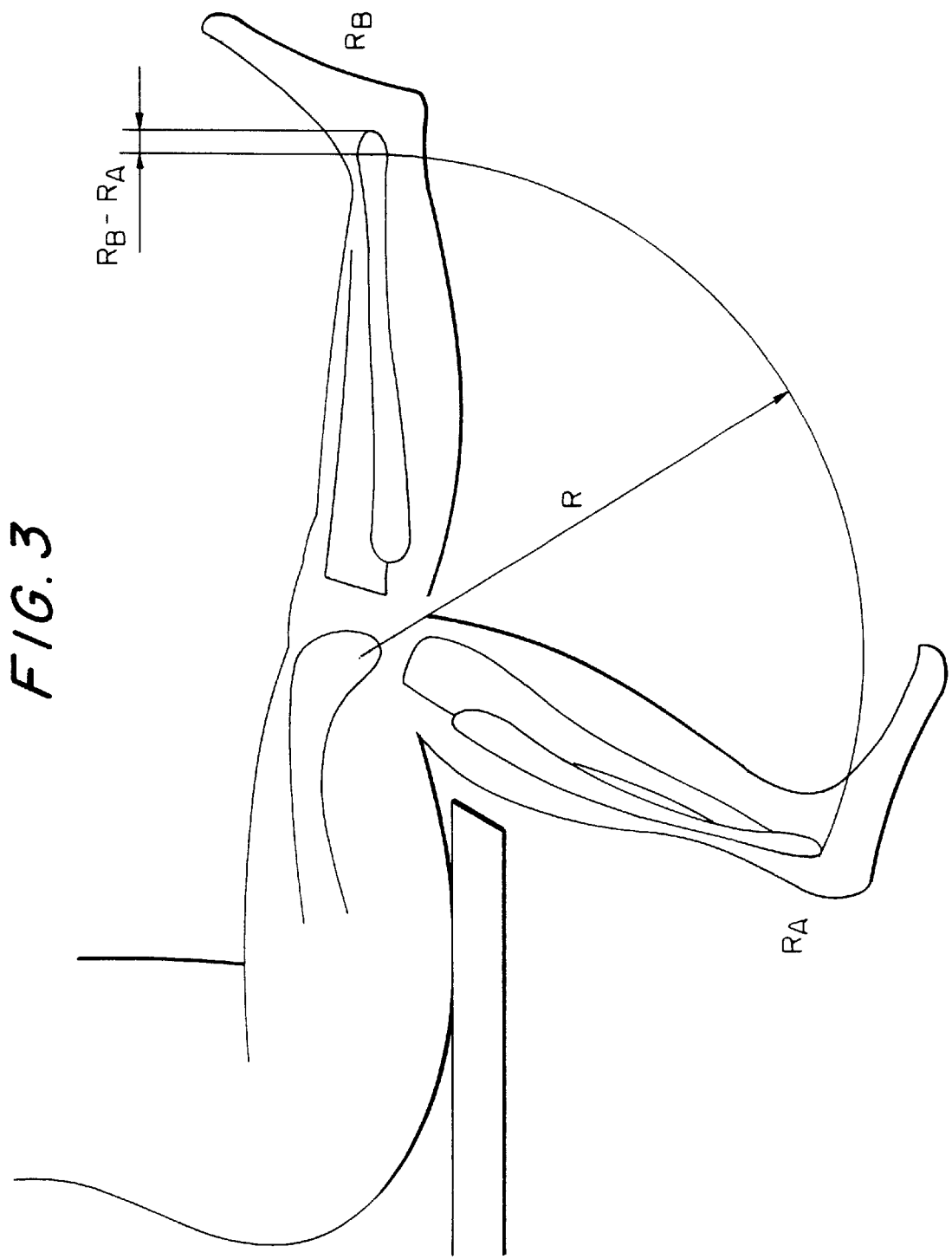
FIG. 3 illustrates the variation in the distance between the femoral condyle and the malleolus which occurs during the extension of the leg.
Figure 4:
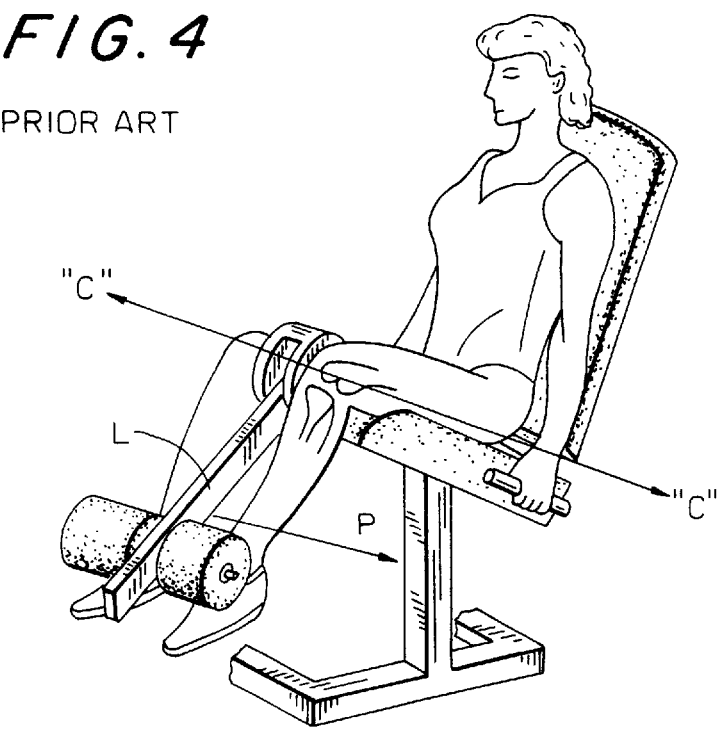
FIG. 4 shows the type of gym machine that exists at present, called leg extension machine, where the load is placed on the mobile arm.
Figure 5:
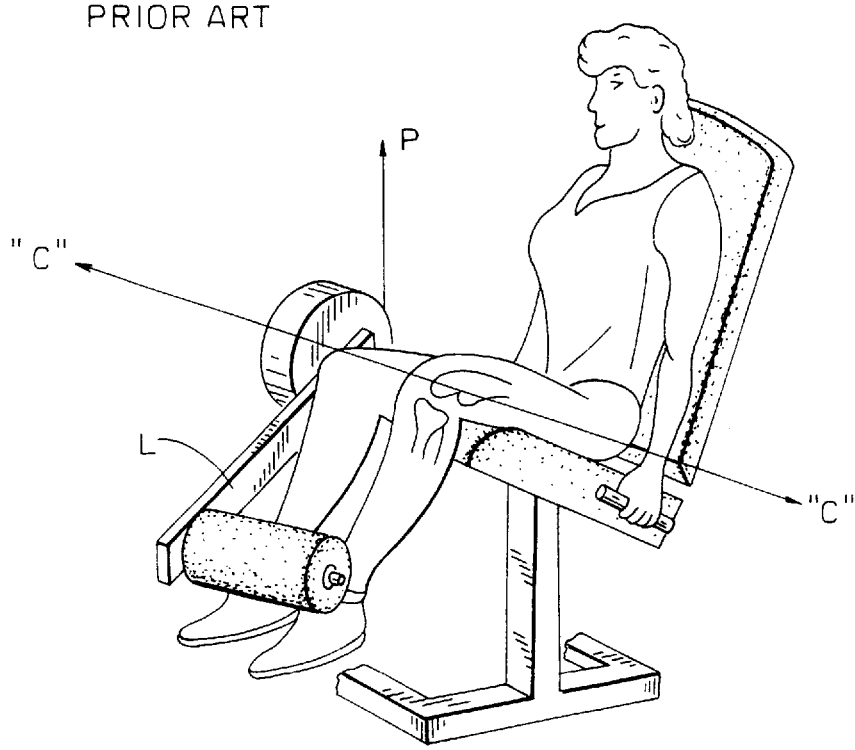
FIG. 5 shows a leg extension machine where the load is placed on the deriver shaft.
Figure 6:
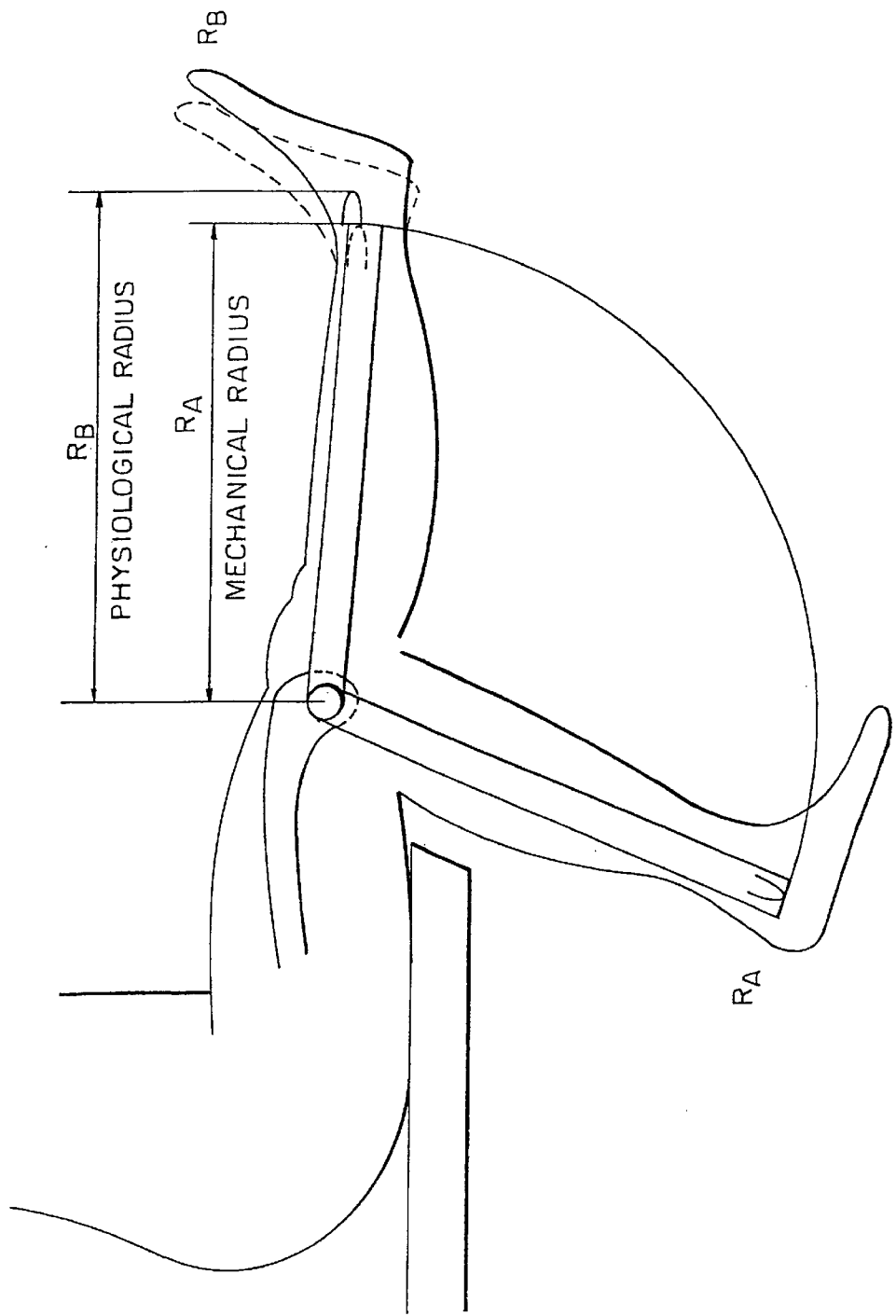
FIG. 6 illustrates the movement of the mobile arm on a leg extension machine.
Figure 7:
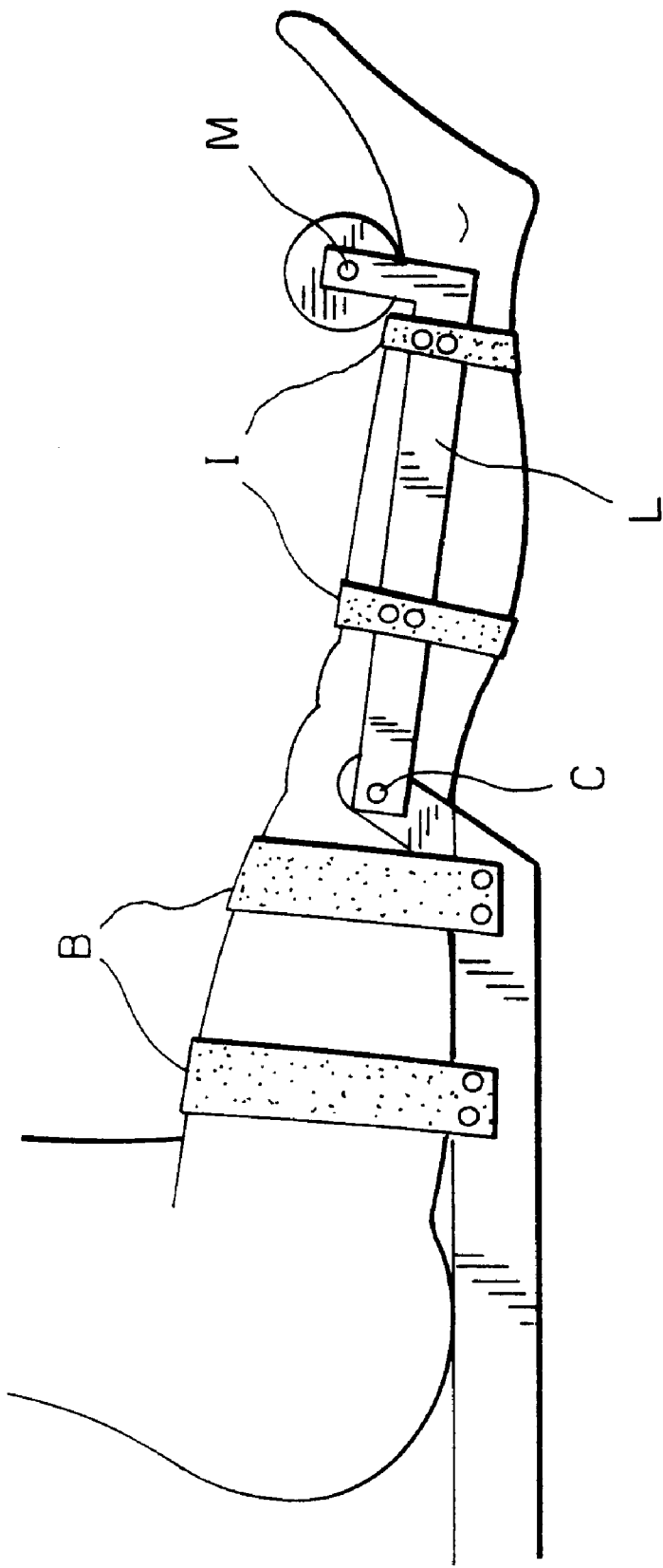
FIG. 7 show the constraints placed on the slinged leg in a leg extension machine.
Figure 8:
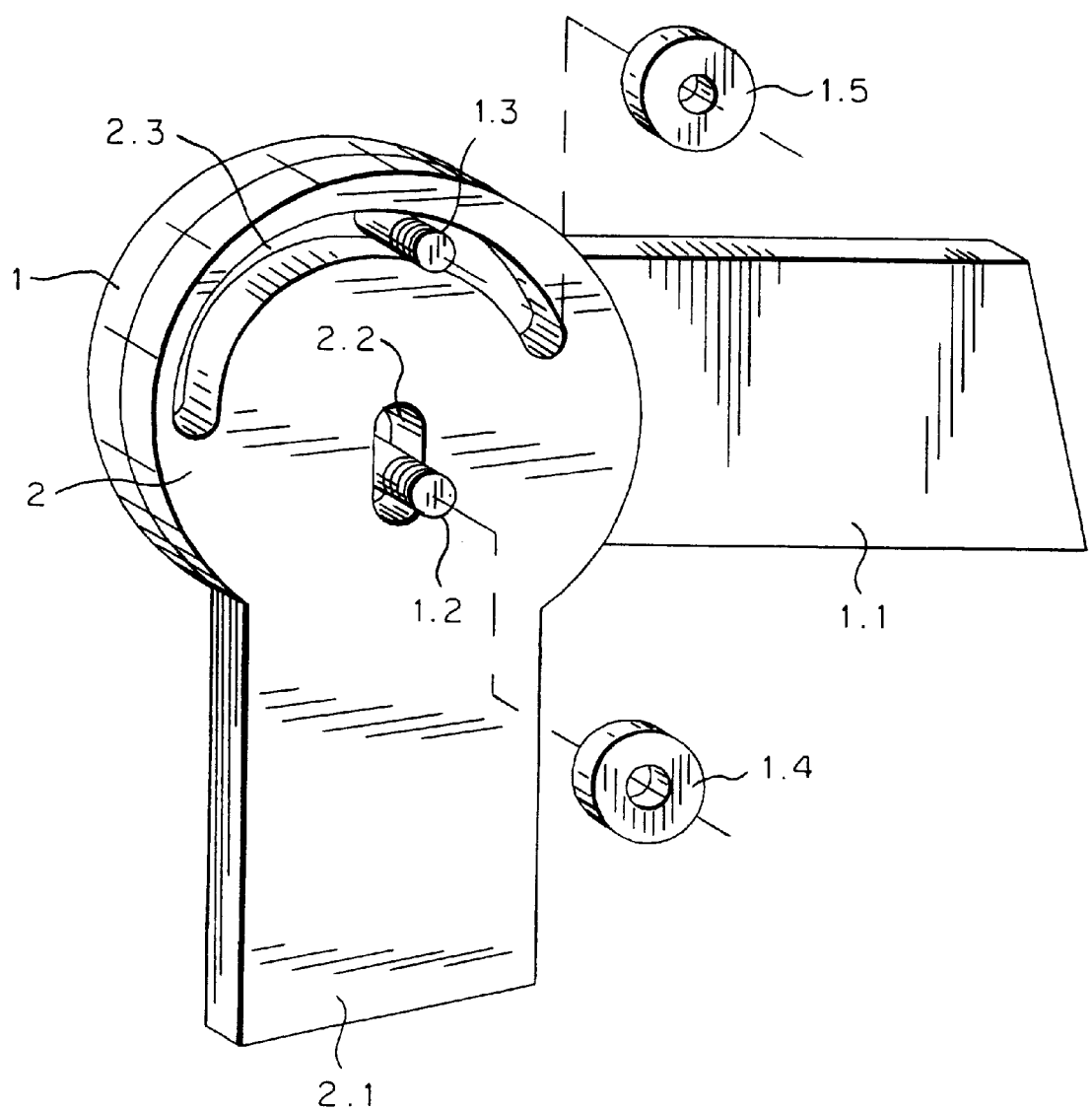
FIG. 8 illustrates a prospective view of the articulated joint object of this patent application featuring only two plates.
Figure 10:
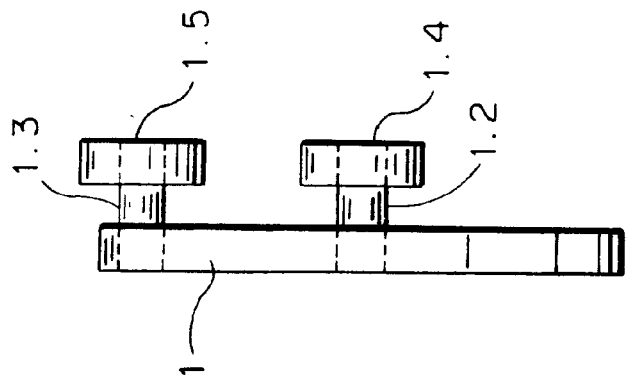
FIG. 10 illustrates a lateral view of the same plate.
Figure 9:
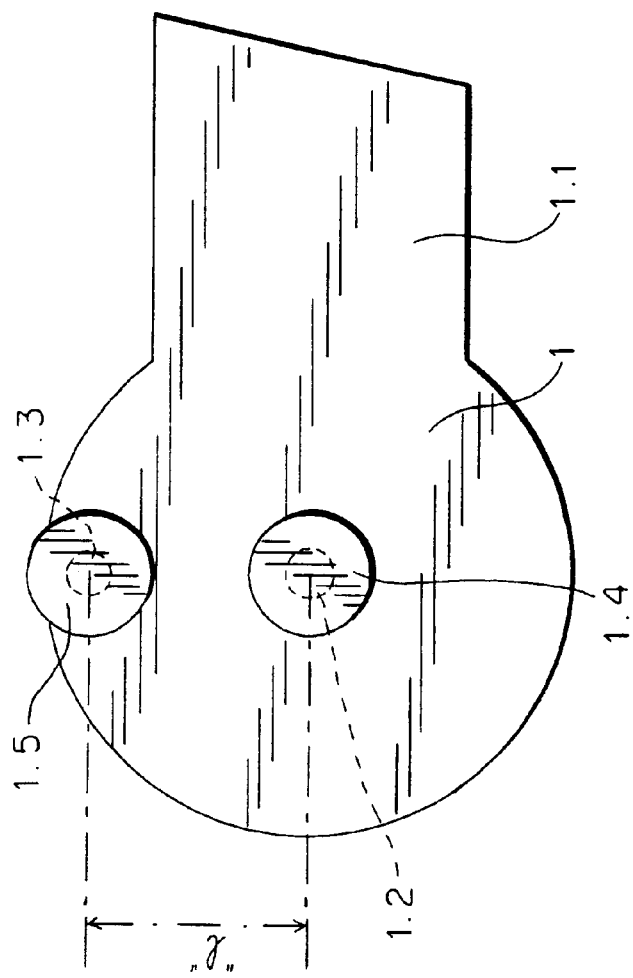
FIG. 9 shows the frontal view of the first of these plates in this articulated joint.
Figure 12:
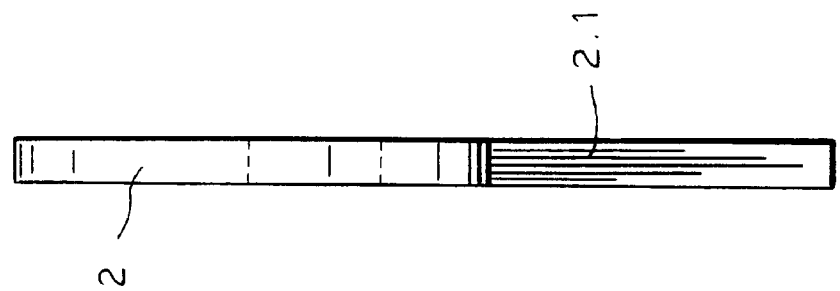
FIG. 12 illustrates a lateral view of the second plate.
Figure 11:
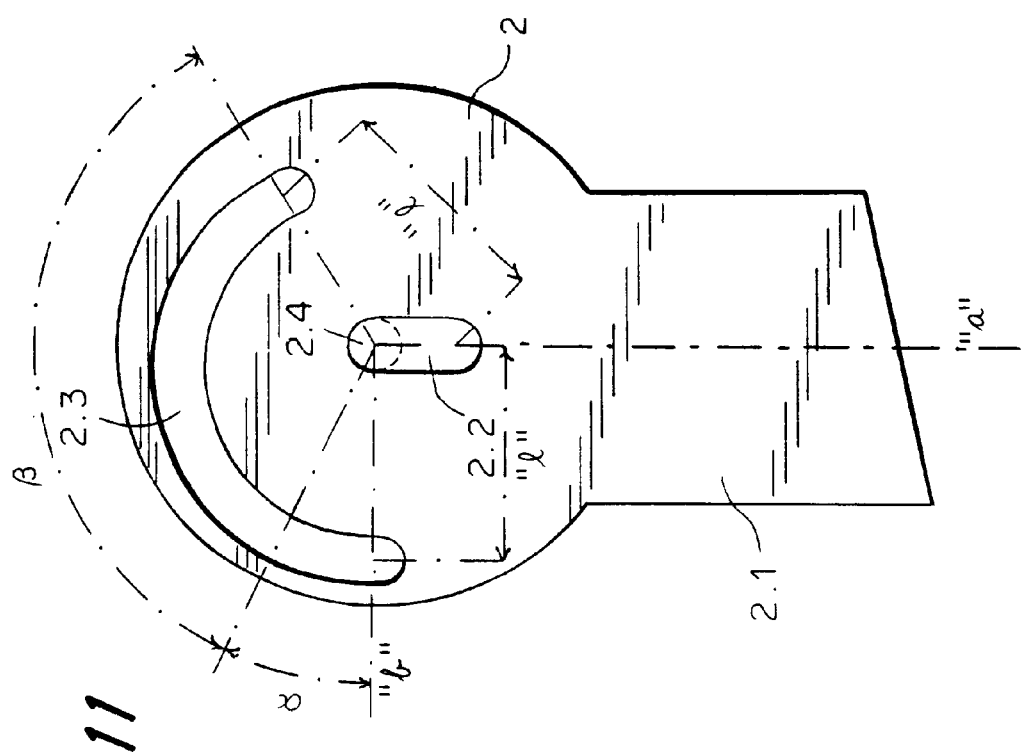
FIG. 11 shows the frontal view of the second of these plates in this articulated joint.
Figure 13:
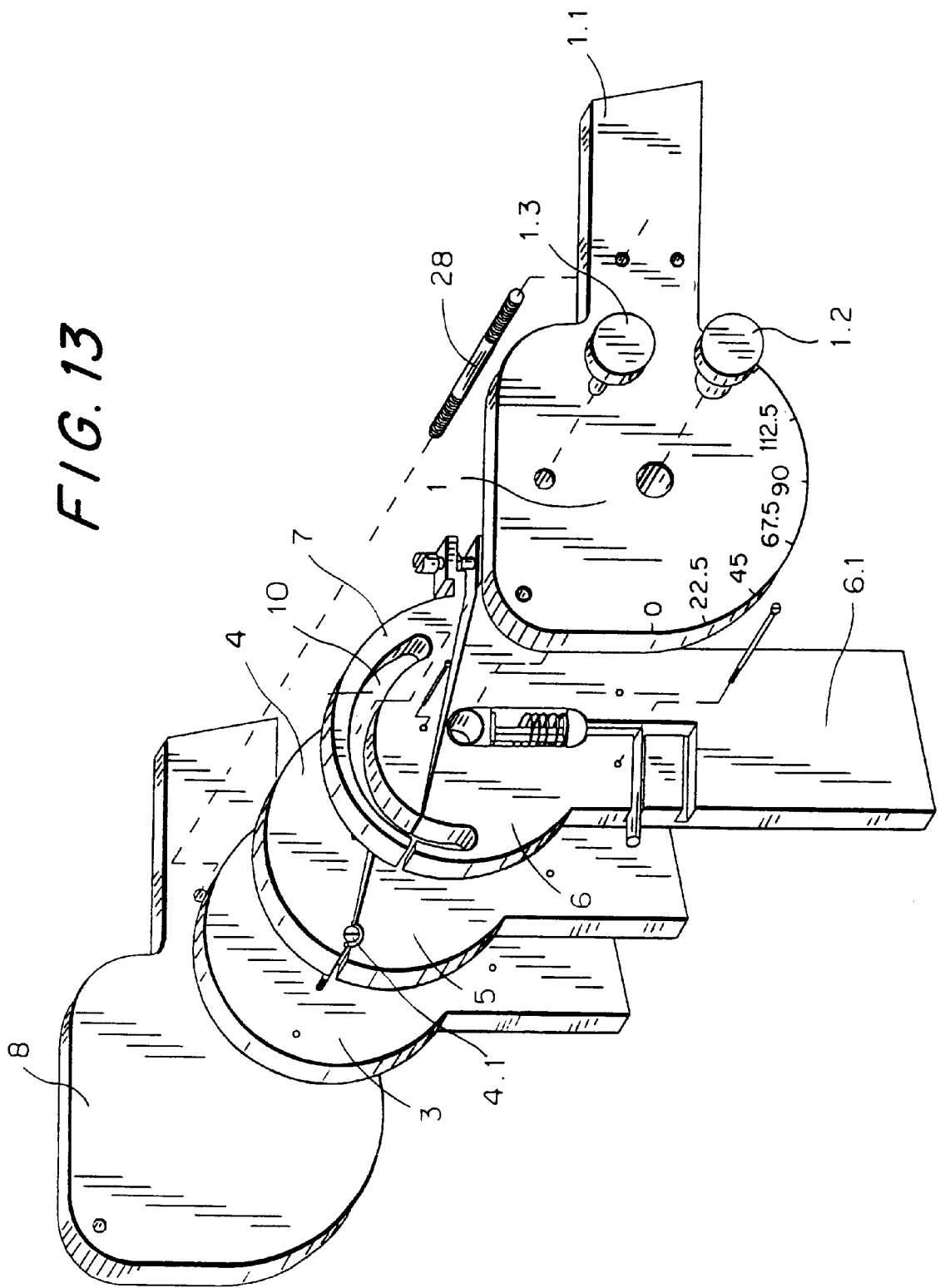
FIG. 13 shows an exploded view of the articulated joint with plates and a group of plates and segments of plates.
Figure 14:
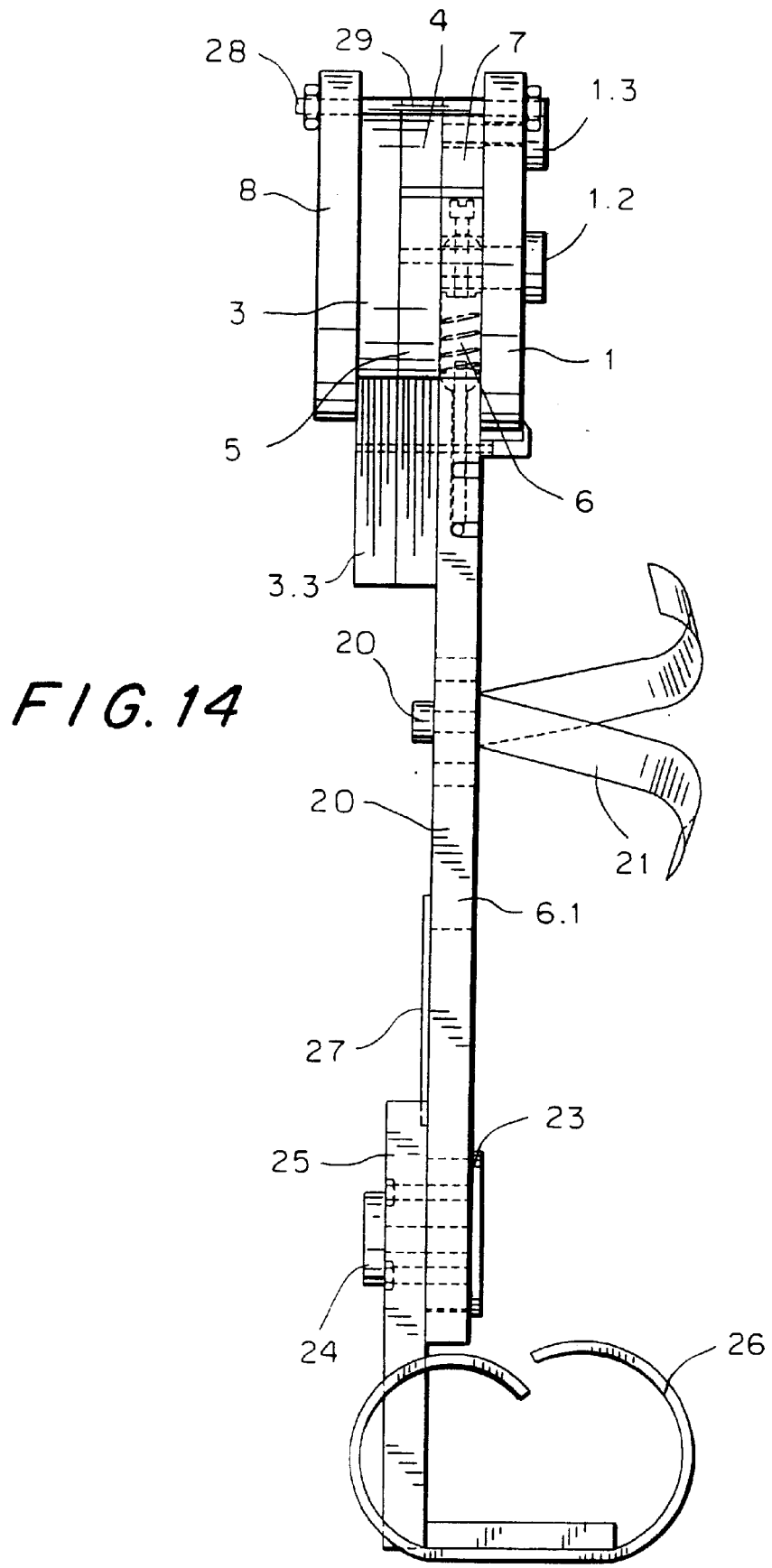
FIG. 14 illustrates a frontal view of the articulated joint and the mobile arm.
Figure 15:
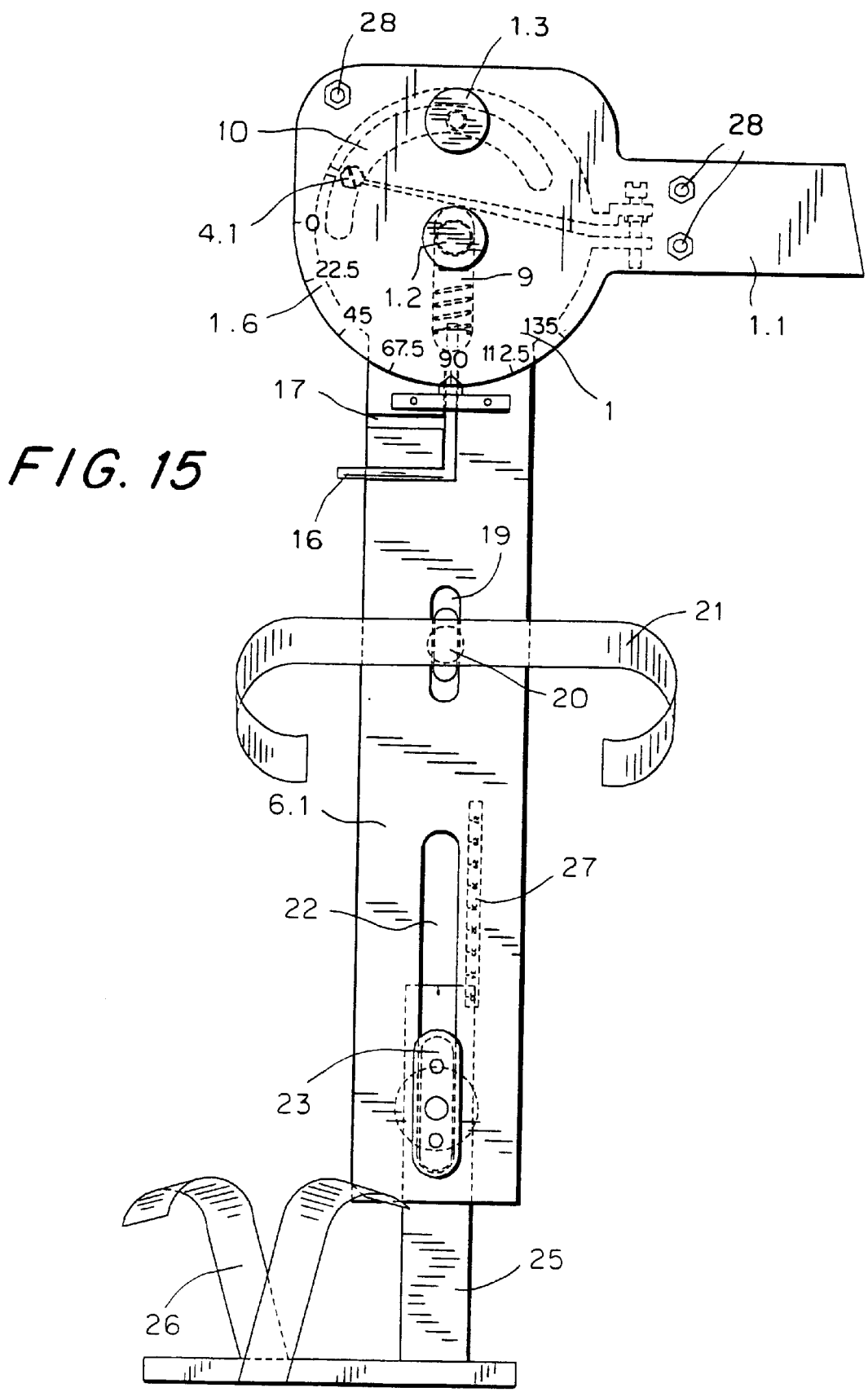
FIG. 15 shows a lateral view of the same articulated joint and its respective mobile arm.
Figure 16:
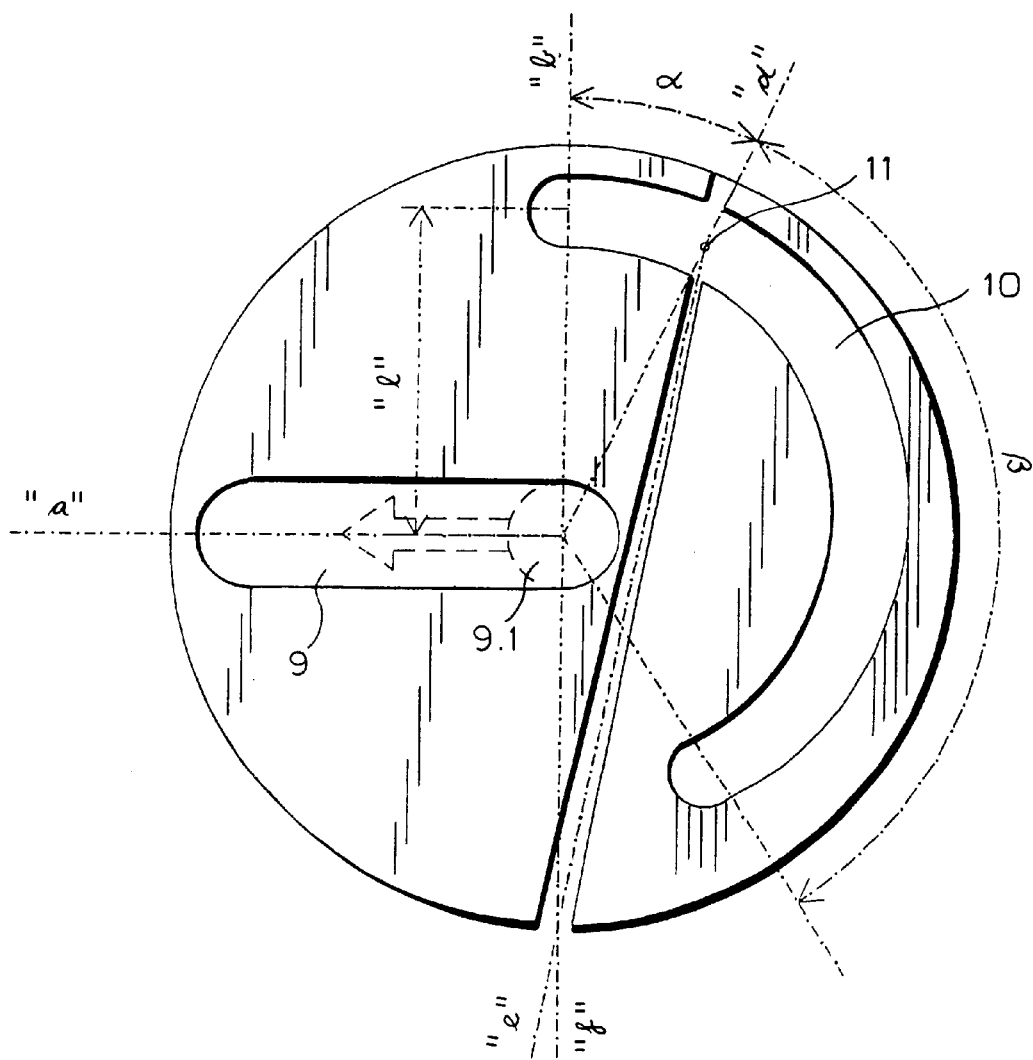
FIG. 16 illustrates the lateral view of the articulated joint and makes its structuring theory explicit.
Figure 18:
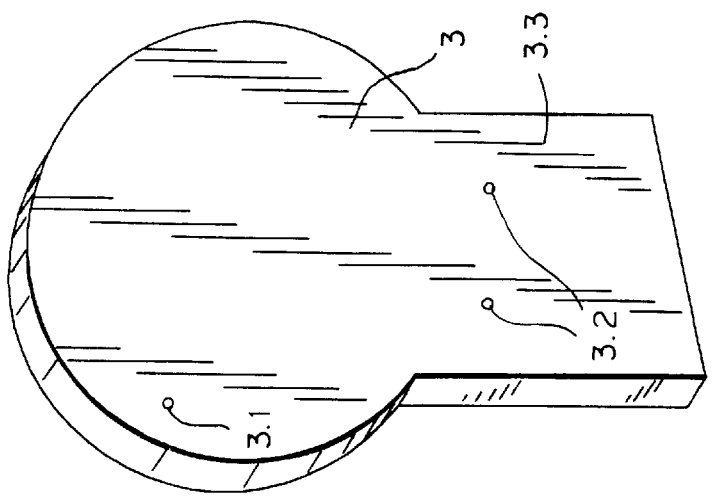
FIG. 18 illustrates the first plate of the mobile group of the articulated joint.
Figure 17:
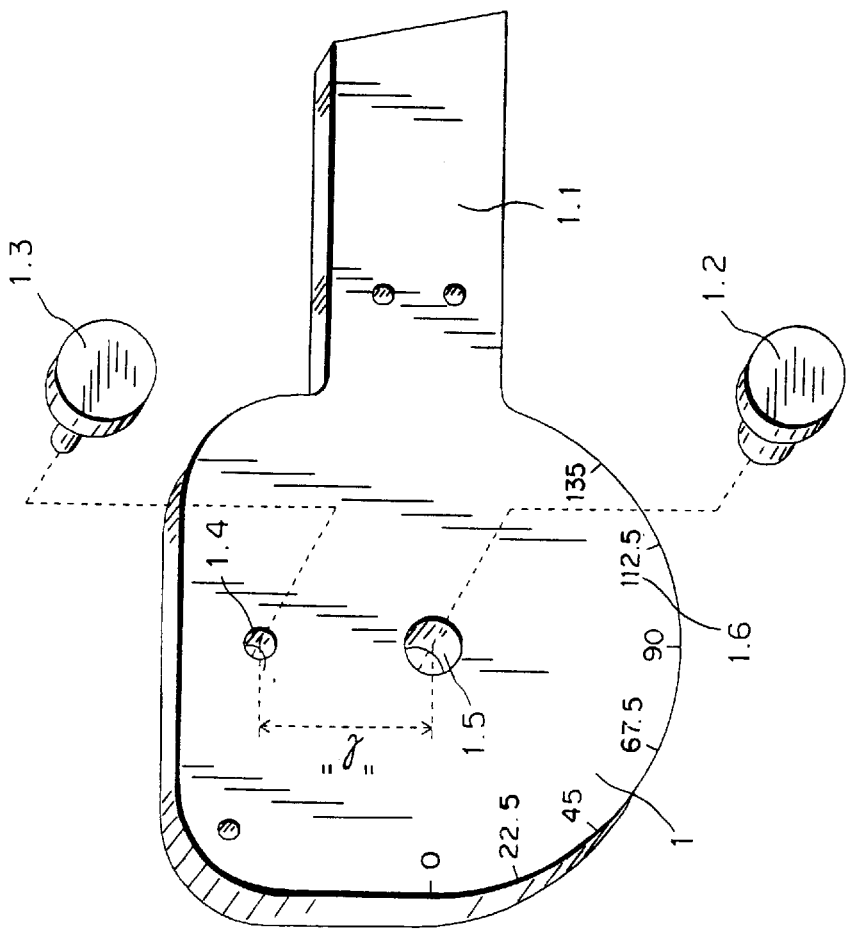
FIG. 17 illustrates a prospective view of the plate of the articulated joint which is connected to the gym machine.
Figure 26:
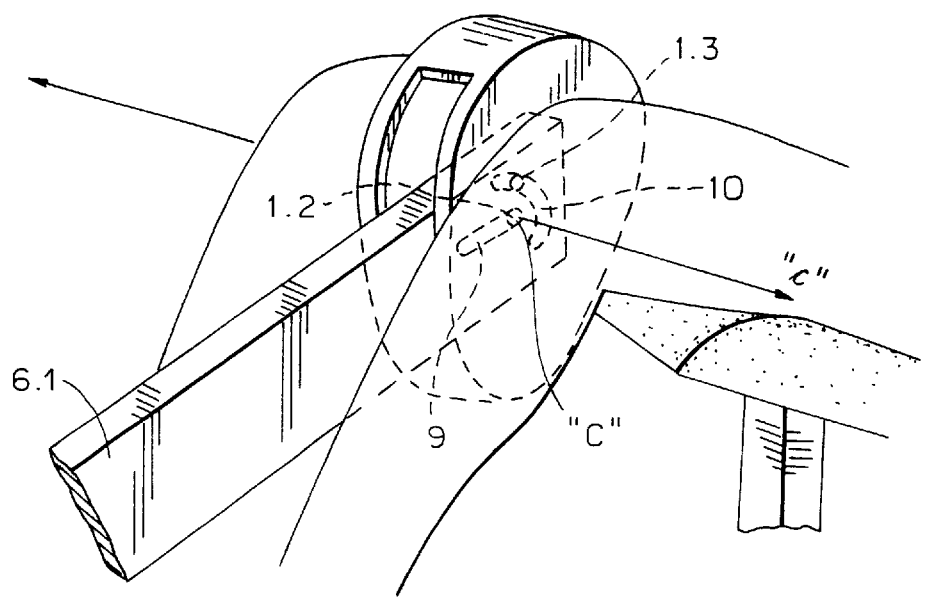
FIG. 26 shows the articulated joint applied to a leg extension machine where the load is placed on the mobile arm.
Figure 27:
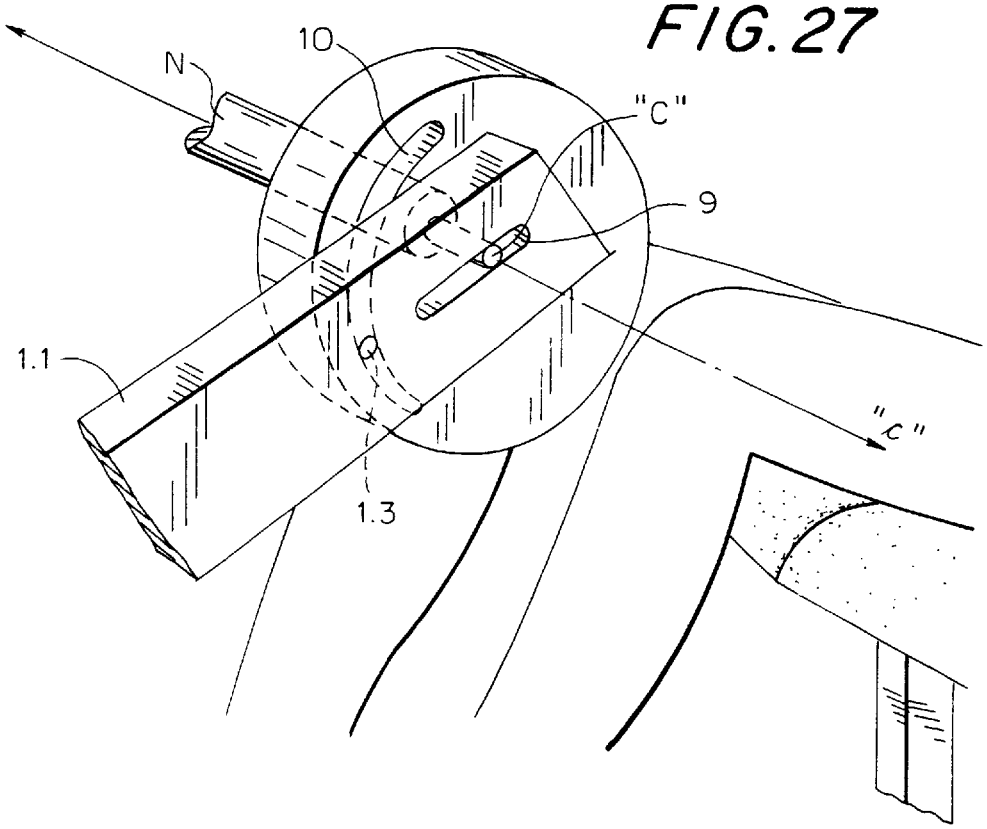
FIG. 27 shows the articulated joint applied to a leg extension machine where the load is placed on the driver shaft of the articulated joint.
Figure 28:
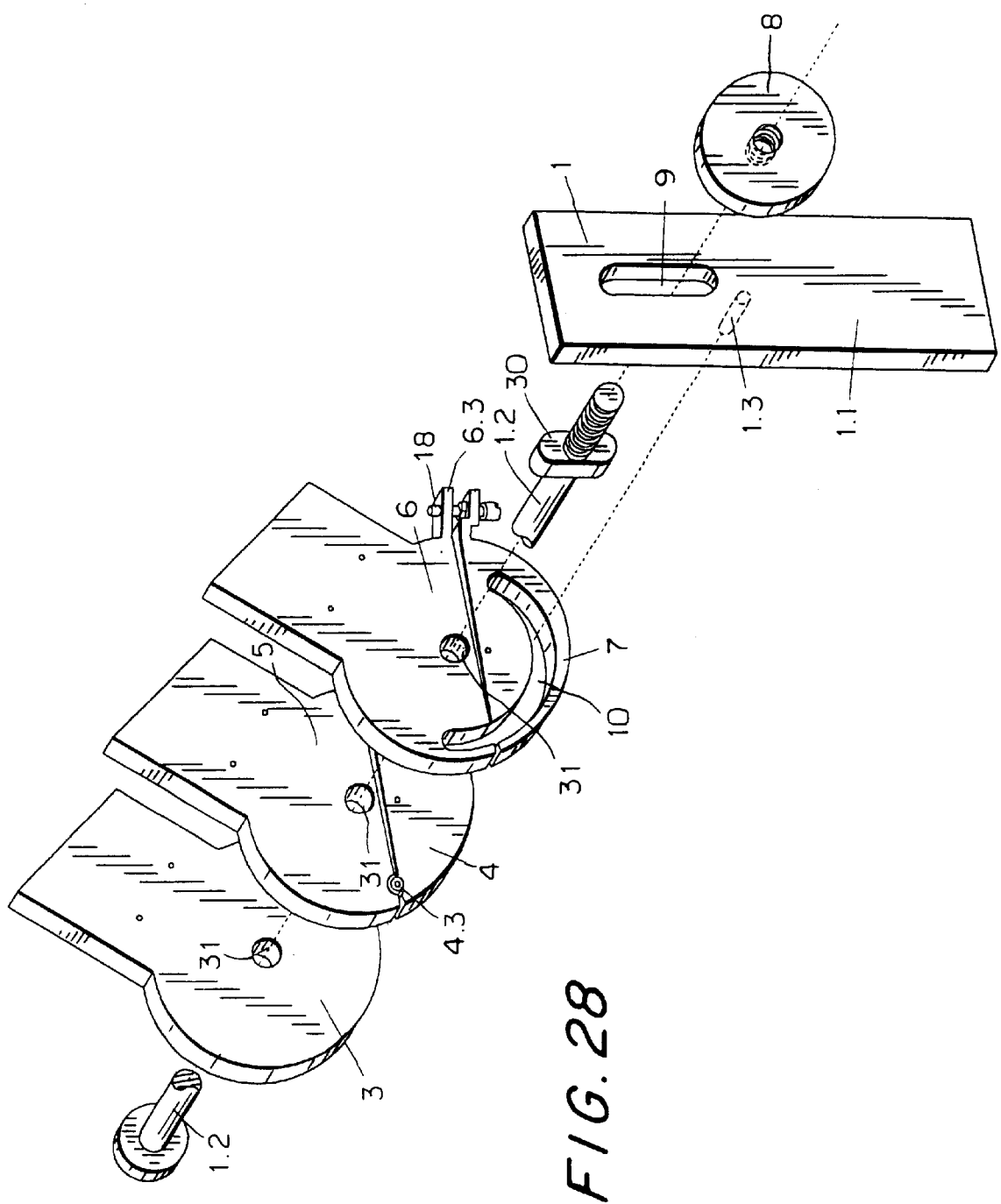
FIG. 28 shows an exploded view of the articulated joint illustrated in FIG. 27.
Figure 29:
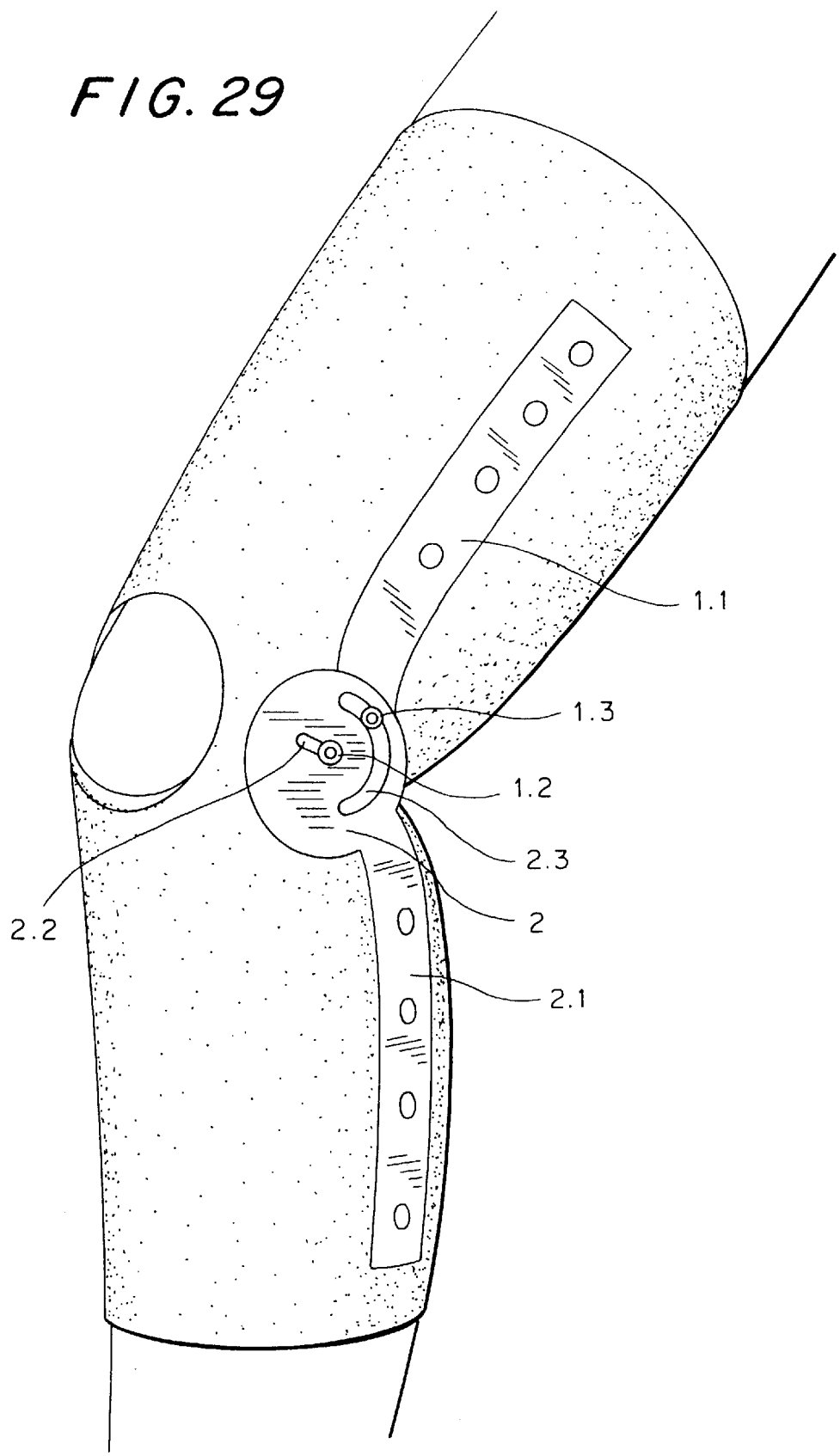
FIG. 29 illustrates a view of a knee tutor featuring the articulated joint which is the object of this patent application.

More precisely in a first, simplified configuration applied to a leg extension gym machine with a load (P) constrained to mobile arm L, the articulated joint is formed by two plates 1 and 2; plate 1 is fastened to the gym machine by means of an arm 1.1, while plate 2 is able to rotate onto plate 1 with reference to a horizontal axis which passes through the femoral condyles of the subject when seated. A mobile arm 2.1, onto which the machine's load is assembled, is fastened to plate 2.

Plate 2 features two openings 2.2 and 2.3 at a right angle to the rotation surfaces of the two plates. The first opening 2.2 is linear in shape; this opening 2.2 begins from a central point 2.4, which is located at the centre of plate 2 and then proceeds towards the mobile arm (2.1) along a radius defined as "a" whose direction coincides with the longitudinal axis of symmetry of mobile arm 2.1 itself.

The ends of the second opening 2.3 located peripherally are shaped like a circle. The centre of one of the ends of this peripheral opening 2.3 is situated at a point located at a distance "I" from the central point 2.4, and lying on radius "b", at a right angle to radius "a", which passes through the central point 2.4 itself and on the same plane. The centre of the other end is located at 135° with reference to the above mentioned radius "b". The peripheral opening 2.3 has a specific shape: initially, for the first 20° (angle α) with reference to the above mentioned radius "b", it is a circumference whose centre coincides with the central point 2.4 and whose radius is equal to "I"; subsequently, for the remaining 115° (angle β), it is a spiral which turns towards the central point 2.4. The sequence of points forming the longitudinal axis of this spiral is derived from the sequence of points of one end of a segment of length "l", the other end moves along the longitudinal axis of the central opening 2.2 (from central point 2.4 radially towards the outside along radius "a").

Plate 1 features two pins 1.2 and 1.3, whose longitudinal axis is at a right angle to the rotation surfaces of plates 1 and 2. These pins are located at a distance equal to "l". Pins 1.2 and 1.3 are cross-through pins and feature distal constraints as plates 1.4 and 1.5 which prevent the two plates 1, 2 from separating.

The subject sits with the flexed leg on a leg extension gym machine built like the machines currently on the market. The thighs are fastened to the seat by belts or other constraints. The subject begins to extend the lower part of the leg, thereby compelling mobile load arm 2.1 to rise.

This compels plate 2 to move. The particular shape of openings 2.2 and 2.3 gives rise to different movements depending on the position of mobile load arm 2.1. During the first phase of the extension (the first 115°: angle β), since peripheral opening 2.3 is shaped like a spiral and the distance between pins 1.2 and 1.3 is still "l", plate 2 will be compelled to endure a twofold movement: rolling and sliding upwards. As plate 2 features the mobile load arm 2.1 the latter follows the movements of plate 2, and therefore translates upwards and rotates at the same time. This movement follows perfectly the movement of the leg fastened to mobile arm 2.1 as the latter makes a spiralling trajectory, like the physiological one of the knee. At each point of the extension, each point of contact between the leg and mobile arm 2.1 corresponds perfectly, thereby avoiding anomalous tensions in the knee.

Subsequently (for the remaining 15°–20° of the extension: angle α), as peripheral opening 2.3 is a circumference whose centre coincides with the centre of central pin 1.2 and with the central point 2.4, plate 2 will simply rotate onto plate 1.

In the return movement the same motions occur but reversed: when the leg flexes there is at first a rotation of plate 2 on plate 1, succeeded by a rolling with a sliding towards the bottom and, lastly, only a translation towards the bottom becoming more and more accentuated.

For the articulated joint to be personalised, and thus suitable for each subject, without having to make changes in plate 2, it is necessary to use an articulated joint more complex.

Indeed, in a second configuration applied to a leg extension gym machine with a load constrained to mobile arm L, plate 2 is replaced by a group composed of a plate 3 and four segments of plates 4, 5, 6, 7, positioned side by side and shaped like a disc or like a fraction of a disc. This plate and segments of plates are connected to one another the group is free to rotate onto plate 1 and onto the last cover plate 8, with reference to a horizontal axis "c", which passes through the femoral condyles of the subject when seated. The segments of plates 4, 5, 6, 7 are arranged in pairs (4,7 and 5,6) where one pair of segments of plates 4, 7 is placed side by side to the other pair of segments of plates 5,6. in each pair one segments of plates 4, 7 is put at the top of the other 5, 6.

Segments of plates 4, 5, 6, 7, are fastened to plate 3, which is the farthest from plate 1 of the group. Plate 3 features a threaded hole 3.1 in correspondence with the fulcrum of segment of plate 4, onto which a pin 4.1 is screwed, allowing the rotation of segment of plate 4 with reference to plate 3. Furthermore, two threaded holes 3.2 are made on plate 3 which lock segments of plates 5, 6 onto plate 3 by means of adequate screws.

Segments of plates 4, 5, 6, 7 are shaped in a specific manner. An examination of the latter two reveals that segment of plate 6 features an linear central opening 9 which is similar to the above mentioned linear central opening 2.2. This opening 9 begins from the central point 9.1, which is located at the centre of the plate divided into segments of plates 6, 7, towards the outside, along a radius defined as "a", which constitutes the longitudinal axis of symmetry of the mobile arm 6.1 featured by segment of plate 6. This mobile arm 6.1 is connected to the weights.

When the two segments of plates 6, 7 are put one at the top of the other they feature a peripheral opening 10, similar to the previously described peripheral opening 2.3.

In peripheral opening 10 an important role is played by radius "d", which divides opening 10 into two parts: one circular part 10.1, located on segment of plate 6 and one spiral part 10.2, located on segment of plate 7. Radius "d" is inclined by 20° (on the same plate) with reference to radius "b". A fulcrum 11 is located on radius "d".

Segments of plates 4, 5, 6, 7 are cut according to an axis "e" which goes from fulcrum 11 to the point of intersection of radius "f" with the outer edge (of segments of plates 4, 5, 6, 7); radius "f" is in a position which is diametrically opposite to radius "b".

Getting back to the details of the various components, it will appear that segment of plate 5 is fastened, as previously described, to plate 3. It features two holes 5.1 through which pass two screws, having the same interaxis as holes 3.2. The side which faces segment of plate 4 features indentation 5.2 which is slightly shorter than half the circumference and whose centre is in fulcrum 11.

Segment of plate 4 is fastened onto plate 3, at the top of segment of plate 5. From the side closest to segment of plate 5 a half cylinder 4.2 (with centre in fulcrum 11) protrudes, its diameter is less than indentation 5.2 of segment of plate 5, so as to allow it to be inserted into the latter and thus permit the rotation between the mechanical members around fulcrum 11. Pin 4.1 is inserted inside hole 4.3, located at the centre of the half cylinder 4.2 (endowed with a countersink 4.4 on the side overlooking segment of plate 7) placed in correspondence with fulcrum 11, around which segment of plate 4 rotates. This rotating pin 4.1 is screwed into hole 3.1 of plate 3. It consists in three parts: head (which is into the countersink 4.4 of the half cylinder 4.2), body (which is smooth and occupies hole 4.3) and thread (which is to be engaged in hole 3.1).

Segment of plate 4 also features a threaded hole 4.5, located in the centre, where a screw fastening segment of plate 7 to the side by side segment of plate 4 itself can be inserted.

Segment of plate 6 is fastened to segment of plate 5 and to plate 3 by means of screws that cross holes 6.2, 5.1 and 3.2. At the centre of segment of plate 6 linear opening 9 opens up, while in the farther end from mobile arm 6.1 in the direction of fulcrum 11, the circular part 10.1 of peripheral opening 10 opens up; the latter originates from radius "b" at a distance "l" from central point 9.1, and develops with a constant radius along a arc until it intersects with radius "d".

Central pin 1.2 is inserted into linear opening 9; the former can be locked in correspondence with central point 9.1. In the channel formed by linear central opening 9 spring 12 is inserted; the latter is withheld by a distal spring-lock 13 (which is crossed lengthwise by a hole) and by proximal spring-lock 14. The latter acts on a bush 15, within which central pin 1.2 is lodged. The latter's internal diameter corresponds to the outer diameter of central pin 1.2 and the outer diameter to the size of linear central opening 9. The mechanical finishing of bush 15 must enable it to rotate freely on central pin 1.2, and to slide freely into central opening 9. Proximal spring-lock 14 can be pushed by a peg 16, which is lodged in mobile arm 6.1 within an indentation 17 that features two locked positions: when one end of peg 16 is inserted in the proximal locked position 17.1 bush 15, pushed from the other end by peg 16 itself (after crossing distal spring-lock 13), is compelled to place itself on central point 9.1; on the other hand, when peg 16 is inserted in the distal locked position 17.2 bush 15 is free to move within central opening 9.

Segment of plate 7 is fastened onto segment of plate 4 by means of a screw which crosses a countersunk hole 7.1 which is to be engaged in hole 4.5. Spiral part 10.2 of peripheral opening 10 is carved onto segment of plate 7; the former extends from radius "d" until the complete development of peripheral opening 10 itself.

Segments of plates 5,6 feature an edge when coincides with a similar edge on segments of plates 4, 7 which is not, however, cut exactly along axis "e" but rather, considering fulcrum 11 to be the starting point of the edge, diverges by a few degrees from axis "e" in the direction of mobile arm 6.1. Segments of plates 4, 7 also feature an edge overlooking segments of plates 5, 6 which is not cut exactly along axis "e" but, unlike the latter plates, and, again, considering fulcrum 11 to be the starting point of the edge, diverges by a few degrees from axis "e" in the opposite direction from mobile arm 6.1.

As the edge of segments of plates 4, 7 and that of segments of plates 5, 6 share the same centre but have sides that open in the opposite direction, a distance is formed where axis "e" intersects with the external edge which permits segments of plates 4 7 to rotate on segments of plates 5, 6; fulcrum 11 is the centre of this rotation movement.

A wing 6.3 and 7.2 is fastened onto segments of plates 6, 7, in proximity to the outer edge. A threaded, cross-through hole 6.4 is featured by wing 6.3, while wing 7.2 features a non threaded cross-through hole (with the same interaxis). A screw 18 is inserted through the latter hole; screw 18 is endowed with a bolt 18.1 which is engaged in hole 6.4. By acting on this screw 18 it is therefore possible to adjust the distance between segments of plates 6, 7 (and, consequently, also between segments of plates 4, 5); it is possible to adjust this distance to the micrometer.

A peripheral pin 1.3, which crosses threaded hole 1.4 (which is on plate 1) is inserted in peripheral opening 10. It is made of three sectors: a handwheel with a knurled edge which makes it easier to lock it manually on plate 1, a threaded sector which is screwed inside hole 1.4, and a non threaded cylinder section which slides inside peripheral opening 10 and protrudes from the side opposite the one featuring the handwheel.

Furthermore, plate 1 also features a second hole 1.5, located centrally, with a longitudinal axis at a right angle to the rotation surfaces of plates 1, 3 and segments of plates 4, 5, 6, 7, and located at a distance equal to "I" with reference to peripheral hole 1.4, within which the central pin 1.2 is inserted. The latter is cross-through and its distal end is lodged inside bush 15, thereby crossing linear central opening 9. Central pin 1.2 also consists in three parts: a handwheel with a knurled edge, a threaded section which is screwed inside hole 1.5, and a non threaded cylinder section which slides inside linear central opening 9.

In the section closer to mobile arm 6.1 lies a linear opening 19 which is rectangular in shape (and which follows the direction of axis "a"), inside which a mechanical system 20 with screws is inserted, allowing this system to move longitudinally along opening 19.

A small, semi rigid belt 21 is fastened onto mechanical system 20 to be tied around the distal part of the belt, approximately below the knee; the possibility to move mechanical system 20 makes it possible to identify the exact point at which this constraint is to be fastened according to the anthropometric dimensions of the user of the invention.

Mobile arm 6.1 also features another linear opening 22, located distally, which is also rectangular in shape (possibly with rounded sides) which follows the direction of axis "a".

A feather key 23 is lodged inside opening 22; externally the former is wider than opening 22 and it is thicker than mobile arm 6.1; however, it is allowed to slide freely along axis "a" of mobile arm 6.1. The foot rest is fastened to feather key 23 by means of screws; a pin 24 fastens feather key 23 to mobile arm 6.1.

The above mentioned foot rest consists in two blades 25 fastened to one another at 90°. The vertical blade allows the connection to mobile arm 6.1 by means of screws which engage in feather key 23; the horizontal blade allows the foot to rest by coming into contact with a large portion of the bottom of the foot.

The foot resting in this location is fastened to blade 25 by means of a small belt 26, so as to maintain the starting position throughout the flexionextension movement.

A degree angular scale 1.6 is drawn at the periphery of plate 1. The 0° position is located in correspondence with radius "a" in the position in which mobile arm 6.1 constitutes the extension of bar 1.1; the scale develops in the opposite direction to the direction of pin 1.3.

A verification linear millimetre scale is located parallel to opening 22. A 0° reference point is drawn on the outer edge of feather key 23.

The 0 of this millimetre scale 27 is located ideally on central point 9.1 and, consequently, the scale only shows values that are higher than a certain level, for instance 30 centimetres. The distance between the central point 9.1 and the millimetre scale 27 is called radius "R".

The above mentioned plate 8 acts as a cover; it is connected to plate 1 by means of three screws 28; these screws 28 are inserted inside a specific spacing bar 29 which prevents plates 1 and 8 from getting excessively close to one another. These two plates 1, 8 are tightly fastened to the group of plate 3 and segments of plates 4, 5, 6, 7, (by means of screws 28), preventing them from being drawn apart from plate 1. The group of plate 3 and segments of plates 4, 5, 6, 7 is allowed to slide onto plates 1, 8 thanks to the use of self-lubricating substances for contacting surfaces.

As previously described, the length of the knee's crossed ligaments and their point of insertion are individual anthropometric characteristics which shape the knee's particular surfaces and which therefore differ from one individual to another. In order to analyse these characteristics and to personalise the articulated joint a functional assessment is the most common approach. In order to carry out a correct assessment it is first of all indispensable for the knee to be placed on the machine in a precise position; that is to say, the axis which crosses the knee, around which the first 15–20° of the flexion-extension take place (axis "c") must correspond perfectly to axis "c" of the device, which crosses the centre of central point 9.1.

This alignment of the centre of both the knee and the machine, called self-centerig, must be performed before any other step and must be performed again every time that the same subject places him/herself on the machine and need to return to the same working conditions.

The subject is made to sit down with his leg on the leg extension machine. The thigh belts and belts 21, 26 on the distal part of the leg are fastened. Mechanical system 20 and pin 24 are released, so that the former may be free to slide into opening 19 and feather key 23 into opening 22.

After removing peripheral pin 1.3 from plate 1 and locking central pin 1.2 in the central position (by means of peg 16 which is located in the proximal locked position 17.1 which locks bush 15 onto central point 9.1), mobile arm 6.1 is used as an arm rotating around a fixed centre (whose centre is central point 9.1 and which is coaxial to axis "c" of the device).

The subject, with leg outstretched, performs some small flexion-extension movements of approximately 30°, readable in the degree angular scale 1.6. If when the user is seated with his limb outstretched radius R differs from the measurement taken when the limb is slightly flexed, the knee is not centred and the latter's axis "c" will not coincide with the axis "c" of the device. For instance, if radius R is greater, the knee is in a forward position with reference to axis "c" which crosses the centre of central point 9.1. If the radius R is less, the knee is behind or below axis "c".

Once the perfect correspondence between axis "c" of the knee and that of the device has been found, it is possible to trace the particular route of the tibia as it rolls and slides onto the femur. Starting from an outstretched position a few readings are taken, particularly in the last 90° of the movement, i.e. as the leg flexes between 45° and 135°.

The measurements to be taken are the flexing angle (to be read on degree scale 1.6) and the corresponding variation of radius R (to be read on linear millimetre scale 27).

Having taken a number of such paired readings, it is possible to compute mathematically the curve interpolating the points read at the maximum flexing and thus identify the spiral part 10.2 of the peripheral opening 10 which best suits the subject being examined.

The subsequent personalisation of this spiral part 10.2 is performed on millimetric screw 18 which is hinged to wings 6.3 and 7.2 of segments of plates 6, 7. By adjusting this screw 18, the distance between segments of plates 6, 7, (and 4, 5) can be adjusted, as a consequence of which the position of spiral part 10.2 of the peripheral opening 10 with reference to circular part 10.1 of the peripheral opening 10 will also be adjusted. Pin 4.1 is the fulcrum of the rotation of spiral part 10.2 of the peripheral opening 10. When spiral part 10.2 has been adjusted to suit the characteristics of the subject being examined, peg 16 is placed in the distal locked position 17.2, thereby releasing bush 15. Peripheral pin 1.3 is then screwed into peripheral hole 1.4 of plate 1, feather key 23 is locked (by means of pin 24) into opening 22 in correspondence with the reference spot of the foot, and mechanical system 20 is locked in opening 19, thereby definitively fastening the distal part of the leg to mobile arm 6.1.

At this stage, having personalised spiral part 10.2, the subject may start performing normal flexion-extension exercises. The movements of the articulated joint with plates 1, 8 and a group of plate 3 and segments of plates 4, 5, 6, 7 will be similar to those of the two plate articulated joint.

The subject starts from a flexed position to perform an extension of the leg from the thigh, thereby compelling mobile load arm 6.1 to rise.

This compels the group of plate 3 and segments of plates 4, 5, 6, 7 to move. The particular shape of linear central openings 9 and peripheral 10 gives rise to different movements depending on the position of mobile load arm 6.1. Indeed, in the first phase of the extension (the first 1150: angle β), since spiral part 10.2 is shaped like a spiral that returns towards the centre of segment of plate 6, and the distance between the two pins is still "I", the group of plate 3 and segments of plates 4, 5, 6, 7 will be compelled to translate upwards and, at the same time, rotate onto plates 1,8. Arm 6.1, which is fastened to segment of plate 6, logically follows these movements. Subsequently (for the remaining 15°–20° of the extension: angle α), as circular part 10.1 of peripheral opening 10 is a circumference whose centre coincides with the central point 9.1, the group of plate 3 and segments of plate 4, 5, 6, 7 will simply rotate onto plates 1, 8: the central point 9.1 acts as a fulcrum.

Alternatively, the following description concerns the configuration of an articulated joint with plates and a group of plates and segments of plates and the load of the machine on the rotating device.

In this case, central pin 1.2 constitutes the end of a shaft with a longitudinal axis placed on the extension of the knee's axis "c". The group of plate 3 and segments of plates 4, 5, 6, 7, maintain the same function (compared to the previous configuration of the joint), even though their position is changed. Plate 3 and segments of plates 5, 6 are locked to the machine; segments of plates 4, 7, being fastened to plate 3 by means of pin 4.1 and by the screw crossing holes 4.5 and 7.1, also remain fastened to the machine, but may rotate partially onto plate 3 and segments of plates 5, 6, thanks to the above mentioned pin 4.1 located on the fulcrum 11.

Plate 1 constitutes the proximal part of mobile arm 1.1 which replaces the mobile arm 6.1 of the previous joint; it features a central opening 9, formerly featured by segment of plate 6. Plate 1/arm 1.1 is free to rotate onto the group of plate 3 and segments of plates 4, 5, 6, 7.

As previously described, central pin 1.2 here constitutes one end of the driver shaft, which features on the other end a feather key 30 which is lodged in the central opening 9 of plate 1. In order to prevent central pin 1.2/driver shaft from slipping out of group of plate 3 and segments of plates 4, 5, 6, 7, the latter is endowed with a threaded area, in proximity to feather key 30, onto which plate 8 is screwed, thereby acting as a cover for the entire system.

Central opening 9 remains unchanged in its engineering, compared to the description made in the first case for segment of plate 6, with the central point 9.1 as the main locating spot. However, the length of this opening is increased vertically according to the size of feather key 30.

Plate 3 and segments of plates 5, 6 are crossed by a central cross-through hole 31 whose centre corresponds to the centre of central point 9.1, where the central pin 1.2/driver shaft is be lodged and allowed to rotate freely.

The motion of the pin 1.2/driver shaft does not affect plate 3 and segments of plates 5, 6, which are fastened to the machine; rather, it transmits this motion to plate 1 by means of feather key 30 which is located in linear central opening 9. The latter, in turn, will follow the motion suggested by the second opening on segments of plates 6, 7, compelled to do so by the presence of the peripheral pin 1.3 that is fastened to plate 1 and lodged in peripheral opening 10.

The invention thus made is subject to several modifications and variations, all of which pertain to the inventive concept. Furthermore, all details may be replaced with other technically equivalent ones.

What is claimed is:

1. An adjustable radius articulated joint for a gym machine and knee tutor, comprising:

first and second cover plates (1, 8) fixed together in spaced relationship, the first cover plate (1) having a femorial arm (1.1) adapted for attachment to the gym machine;

a first plate (6) having a distal arm (6.1), a second plate (5) and a third plate (3) all fixed together to rotate between the first and second cover plates (1, 8);

wherein the first plate (6) and the second plate (5) each have a segment (4,7) put on the top and fixed together to rotate on the third plate (3);

the segment (7) of the first plate (6) having a first slot (10) continuing into the first plate (6); a center pin (1.2) fixed to the first cover plate (1) for the first, second and third plates (6,5,3) and for the segments (4,7);

the first cover plate (1) having a peripheral pin (1.3) inserted in a peripheral hole (1.4) slidably engaged in the first slot (10); and an adjustment screw (18) engaged between the first plate (6) and the segment of the first plate (6) to personalize the joint for use on a knee of a user.

2. The articulated joint according to claim 1, wherein the segment (7) of the first plate (6) and the segment (4) of the second plate (5) rotate together on a pin (4.1) fixed to the third plate (3) around a fulcrum (11) on the segment (4) of the second plate (5).

3. The articulated joint according to claim 1, further comprising:

a second slot (9) provided on the first plate (6) extending from a center (9.1) of the first plate (6), along a longitudinal axis of the distal arm (6.1) of the first plate (6);

the center pin (1.2) rotatably engaged in a bushing (15) located in the second slot (9);

spring-lock means (13, 14, 15, 16) having a spring (12) engaged in the second slot (9) against the bushing (15) for fixing the bushing (15) at the center (9.1) of the first plate (6) when fixed at a first position and permitting the bushing to slide in the second slot (9) against the spring (12) when fixed at a second position.

4. The articulated joint according to claim 3, wherein the spring-lock means (13, 14, 15, 16) comprises the spring (12) engaged against a first end portion (13) and a second end portion (14), and a peg (16);

the peg (16) slidably extending through the first end portion (13) to press the second portion (14) against bushing (15) in the first position when the peg (16) is secured in a first: notch (17.1) on the first plate (6), and wherein, when the peg (16) is secured in a second notch (17.2) on the first plate (6) in the second position the bushing (15) can slide in the second slot (9).

5. The articulated joint according to claim 3, wherein a belt (21) is fixed adjustably along the longitudinal axis of the distal arm (6.1) adapted to constrain a calf of a user against the distal arm (6.1).

6. The articulated joint according to the claim 3, wherein the distal arm (6.1) features a rectangular opening (22) located distally which develops along the longitudinal axis "a" inside which a feather key (23) is lodged, fixed adjustably along the rectangular opening (22) by means of a pin (24); a foot rest (25) is blocked by the feather key (23); the foot rest (25) having a belt (26) adapted to constrain a foot of the user on the foot rest (25).

7. The articulated joint according to claim 6, wherein a linear scale (27) is provided along an edge of the distal arm (6.1) opposite an adjustment distance of the footrest (25) on the distal arm, a zero point of the linear scale (27) corresponding to the center (9.1) of the first plate (6).

8. The articulated joint according to claim 3, wherein a degree angular scale (1.6) is provided along the periphery of the first cover plate (1) to indicate an angle between the longitudinal axis of the femorial arm (1.1) and the longitudinal axis of the distal arm (6.1).

9. The articulated joint according to claim 1, wherein the adjustment screw (18) is inserted through a through hole in a first wing (7.2) on the segment (7) of the first plate (6) and held in the through hole by a bolt (18.1), wherein when the adjustment screw (18) is threaded in a threaded hole on a second wing (6.3) on the first plate (6) a distance between the first and second wings is adjusted.

10. The articulated joint according to claim 1, wherein the first plate (6), the second plate (5) and the third plate (3) are formed as a single unit.

11. The articulated joint according to claim 1, wherein the segments (4, 7) of the first plate (6) and the second plate (5) are formed as a single unit.

12. The articulated joint according to the claim 1, wherein the first slot (10) has a specific shape; initially for the first 15°–45° has a circular form, whose center coincides with the center point (9.1) with a radius equal to "I"; subsequently, for the remaining 90°–120°, it forms a spiral which develops towards the center point (9.1); one end of the first slot (10) lies on a radius "b"; that is at the right angle to radius "a"; the center point (9.1) is one end of the second slot (9); the other end of the first slot (10) is locatred at the distance "I" from the other end of the second slot (9).

13. The articulated joint according to claim 12, wherein a radius "d"—that is inclined by 15°–45° with reference to radius "b"—divides the first slot (10) in two parts; a circular part (10.1) located on the first plate (6) and a spiral part (10.2) located on the segment (7) of the first plate (6); and a fulcrum (11) is located on radius "d".

14. The articulate joint according to claim 12, wherein the above-mentioned pins (1.2, 1.3) are located at the distance equal to "I".

15. The articulate joint according to claim 12, wherein the first cover plate has a central hole (1.5) located at the distance equal to "I" from the peripheral hole (1.4).

16. The articulate joint according to claim 12, wherein: the first and second plates each have a periphery; the first plate is spaced from the segment of the first plate, and the second plate is spaced from the segment of the second plate along an axis "e" which goes from a fulcrum (11) to the point where a radius "f" intersects the peripheries of the first and second plates; the radius "f" is diametrically opposite to radius "b"; the first plate, the segment of the first plate, the second plate and the segment of the second plate each has an edge that extends generally along the axis "e", but the edge of the first plate deverges from the edge of the segment of the first plate by a few degrees and the edge of the second plate deverges from the edge of the segment of the second plate, by a few degrees, starting from the fulcrum (11) and ending at the peripheries of the first and second plates, so that a distance is created between the first plate and the segment of the first plate and between the second plate and the segment of the second plate adjacent the intersection of axis "e" with radius "f".

17. The articulated joint according to claim 1, wherein the movement of rotation of the joint arises around axis "c", at a right angle to the rotation surfaces of the joint itself.

* * * * *